United States Patent
Stern et al.

(10) Patent No.: US 7,481,809 B2
(45) Date of Patent: *Jan. 27, 2009

(54) HANDPIECE WITH RF ELECTRODE AND NON-VOLATILE MEMORY

(75) Inventors: Roger A. Stern, Cupertino, CA (US); Bryan Weber, Livermore, CA (US); Mitchell Levinson, Pleasanton, CA (US)

(73) Assignee: Thermage, Inc., Hayward, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/158,286

(22) Filed: Jun. 20, 2005

(65) Prior Publication Data

US 2006/0025837 A1    Feb. 2, 2006

Related U.S. Application Data

(63) Continuation of application No. 10/404,414, filed on Mar. 31, 2003, now abandoned, which is a continuation-in-part of application No. 10/400,187, filed on Mar. 25, 2003, now Pat. No. 7,229,436, which is a continuation-in-part of application No. 10/072,475, filed on Feb. 6, 2002, now Pat. No. 7,022,121, and a continuation-in-part of application No. 10/072,610, filed on Feb. 6, 2002, now Pat. No. 7,141,049, which is a continuation-in-part of application No. 09/522,275, filed on Mar. 9, 2000, now Pat. No. 6,413,255, application No. 10/400,187, which is a continuation-in-part of application No. 10/026,870, filed on Dec. 20, 2001, now Pat. No. 6,749,624, which is a continuation of application No. 09/337,015, filed on Jun. 30, 1999, now Pat. No. 6,350,276, and a continuation-in-part of application No. 08/942,274, filed on Sep. 30, 1997, now Pat. No. 6,425,912, and a continuation-in-part of application No. 08/914,681, filed on Aug. 19, 1997, now Pat. No. 5,919,219, and a continuation-in-part of application No. 08/827,237, filed on Mar. 28, 1997, now Pat. No. 6,430,446, which is a continuation-in-part of application No. 08/583,815, filed on Jan. 5, 1996, now Pat. No. 6,241,753.

(60) Provisional application No. 60/123,440, filed on Mar. 9, 1999.

(51) Int. Cl.
A61B 18/18 (2006.01)

(52) U.S. Cl. .............................. 606/41; 606/34; 606/48

(58) Field of Classification Search ........... 607/96–102; 606/32–52

See application file for complete search history.

(56) References Cited

U.S. PATENT DOCUMENTS 2,716,698 A    8/1955    Brukner (Continued)

FOREIGN PATENT DOCUMENTS

CA    1228401    10/1987

(Continued)

OTHER PUBLICATIONS

Allain, et al., *Isometric Tensions Developed the Hydrothermal Swelling of Rat Skin*, Connective Tissue Research, vol. 7, pp. 697-701 (1990).

(Continued)

*Primary Examiner*—Henry M Johnson, III
(74) *Attorney, Agent, or Firm*—Wood, Herron & Evans, LLP

(57) ABSTRACT

An RF device includes a support structure coupled to an RF electrode that has conductive and dielectric portions. A cooling member is coupled to the support structure and is configured to cool a back surface of the RF electrode. The cooling member is distanced from the back surface of the RF electrode. A memory is coupled to the RF electrode. The memory is configured to store information to facilitate operation of at least one of the RF electrode, the cooling member and an RF energy source.

20 Claims, 13 Drawing Sheets

U.S. PATENT DOCUMENTS

| | | | |
|---|---|---|---|
| 2,954,771 A | 10/1960 | Boyan | |
| 3,327,712 A | 6/1967 | Le et al. | |
| 3,354,884 A | 11/1967 | Rudo | |
| 3,658,051 A | 4/1972 | MacLean | |
| 3,693,623 A | 9/1972 | Amstutz et al. | |
| 3,760,807 A | 9/1973 | Neefe | 604/294 |
| 3,800,802 A | 4/1974 | Lipsky et al. | |
| 3,818,129 A | 6/1974 | Yamamoto | |
| 3,831,604 A | 8/1974 | Neefe | |
| 3,834,391 A | 9/1974 | Block | |
| 3,848,600 A * | 11/1974 | Patrick et al. | 606/32 |
| 3,930,504 A | 1/1976 | de Laforcade | |
| 3,970,088 A | 7/1976 | Morrison | |
| 3,991,700 A | 11/1976 | Cleary et al. | |
| 4,014,343 A | 3/1977 | Esty | |
| 4,074,718 A | 2/1978 | Morrison | |
| 4,093,975 A | 6/1978 | Roberts | |
| 4,140,130 A | 2/1979 | Storm, III | |
| 4,164,226 A | 8/1979 | Tapper | |
| 4,186,729 A | 2/1980 | Harrison | |
| 4,210,152 A | 7/1980 | Berry | |
| 4,229,658 A | 10/1980 | Gonser | |
| 4,233,498 A | 11/1980 | Payne et al. | |
| 4,283,661 A | 8/1981 | Doty | |
| 4,290,435 A | 9/1981 | Waggott | |
| 4,298,005 A | 11/1981 | Mutzhas | |
| 4,304,235 A * | 12/1981 | Kaufman | 606/32 |
| 4,315,503 A | 2/1982 | Ryaby et al. | |
| 4,316,474 A | 2/1982 | Spethmann | |
| 4,321,930 A | 3/1982 | Jobsis et al. | |
| 4,343,301 A | 8/1982 | Indech | |
| 4,346,715 A | 8/1982 | Gammell | |
| 4,366,570 A | 12/1982 | Bees | |
| 4,375,220 A | 3/1983 | Matvias | |
| 4,380,240 A | 4/1983 | Jobsis et al. | |
| 4,381,007 A | 4/1983 | Doss | 606/5 |
| 4,387,714 A * | 6/1983 | Geddes et al. | 606/32 |
| 4,388,924 A | 6/1983 | Weissman et al. | |
| 4,441,486 A | 4/1984 | Pounds | |
| 4,444,190 A | 4/1984 | Mutzhas | |
| 4,462,412 A | 7/1984 | Turner | |
| 4,497,018 A | 1/1985 | Rice | |
| 4,506,196 A | 3/1985 | Bees | |
| 4,522,210 A | 6/1985 | Simonin | |
| 4,527,550 A | 7/1985 | Ruggera et al. | |
| 4,539,987 A | 9/1985 | Nath et al. | |
| 4,545,368 A | 10/1985 | Rand et al. | |
| 4,556,070 A | 12/1985 | Vaguine et al. | |
| 4,564,011 A | 1/1986 | Goldman | |
| 4,589,423 A | 5/1986 | Turner | |
| 4,645,980 A | 2/1987 | Yang | |
| 4,647,830 A | 3/1987 | Bees | |
| 4,653,495 A | 3/1987 | Nanaumi | |
| 4,669,468 A * | 6/1987 | Cartmell et al. | 606/32 |
| 4,671,286 A | 6/1987 | Renault | |
| 4,672,969 A | 6/1987 | Dew | |
| 4,676,258 A | 6/1987 | Inokuchi et al. | |
| 4,702,732 A | 10/1987 | Powers et al. | 604/20 |
| 4,709,701 A | 12/1987 | Weber | |
| 4,726,377 A | 2/1988 | Jegers et al. | |
| 4,729,375 A | 3/1988 | Jegers et al. | |
| 4,733,660 A | 3/1988 | Itzkan | |
| 4,756,310 A | 7/1988 | Bitterly | |
| 4,775,361 A | 10/1988 | Jacques et al. | |
| 4,779,593 A | 10/1988 | Kiernan | |
| 4,793,325 A | 12/1988 | Cadossi et al. | |
| RE32,849 E | 1/1989 | Wei et al. | |
| 4,798,215 A | 1/1989 | Turner | |
| 4,799,479 A | 1/1989 | Spears | 606/28 |
| 4,810,658 A | 3/1989 | Shanks et al. | |
| 4,829,262 A | 5/1989 | Furumoto | |
| 4,835,749 A | 5/1989 | Welton | |
| 4,838,850 A | 6/1989 | Rosengart | |
| 4,839,562 A | 6/1989 | Francis et al. | |
| 4,851,738 A | 7/1989 | Yang | |
| 4,860,744 A | 8/1989 | Johnson et al. | |
| 4,881,543 A | 11/1989 | Trembly et al. | |
| 4,884,568 A | 12/1989 | Hahn | |
| 4,887,614 A | 12/1989 | Shirakami et al. | |
| 4,889,122 A | 12/1989 | Watmough et al. | |
| 4,901,720 A | 2/1990 | Bertrand | |
| 4,907,589 A | 3/1990 | Cosman | |
| 4,938,221 A | 7/1990 | Tuffel | |
| 4,944,302 A | 7/1990 | Hernandez et al. | |
| 4,947,859 A | 8/1990 | Brewer et al. | |
| 4,957,480 A | 9/1990 | Morenings | |
| 4,962,761 A | 10/1990 | Golden | |
| 4,974,587 A | 12/1990 | Turner et al. | |
| 4,976,709 A | 12/1990 | Sand | |
| 5,003,991 A | 4/1991 | Takayama et al. | |
| 5,008,579 A | 4/1991 | Conley et al. | |
| 5,011,483 A | 4/1991 | Sleister | |
| 5,012,816 A | 5/1991 | Lederer | |
| 5,020,995 A | 6/1991 | Levy | |
| 5,038,780 A | 8/1991 | Boetzkes | |
| 5,054,488 A | 10/1991 | Muz | |
| 5,057,104 A | 10/1991 | Chess | 606/9 |
| 5,059,192 A | 10/1991 | Zaias | |
| 5,066,293 A | 11/1991 | Furumoto | |
| 5,071,422 A | 12/1991 | Watson et al. | |
| 5,083,093 A | 1/1992 | Adler et al. | |
| 5,085,227 A | 2/1992 | Ramon | |
| 5,097,844 A | 3/1992 | Turner | |
| 5,113,462 A | 5/1992 | Clancy et al. | |
| 5,125,922 A | 6/1992 | Dwyer et al. | |
| 5,126,621 A | 6/1992 | Morton et al. | |
| 5,133,351 A | 7/1992 | Masaki | |
| 5,143,063 A | 9/1992 | Fellner | |
| 5,186,181 A | 2/1993 | Franconi et al. | |
| 5,190,517 A | 3/1993 | Zieve et al. | |
| 5,194,723 A | 3/1993 | Cates et al. | |
| 5,218,569 A | 6/1993 | Banks | |
| 5,226,107 A | 7/1993 | Stern et al. | |
| 5,230,334 A | 7/1993 | Klopotek | |
| 5,249,575 A | 10/1993 | DiMino et al. | |
| 5,269,778 A | 12/1993 | Rink et al. | |
| 5,281,798 A | 1/1994 | Hamm et al. | |
| 5,282,797 A | 2/1994 | Chess | |
| 5,290,273 A | 3/1994 | Tan | |
| 5,290,274 A | 3/1994 | Levy et al. | |
| 5,304,169 A | 4/1994 | Sand | |
| 5,312,395 A | 5/1994 | Tan et al. | |
| 5,315,994 A | 5/1994 | Guibert et al. | |
| 5,320,618 A | 6/1994 | Gustafsson | |
| 5,328,488 A | 7/1994 | Daikuzono | |
| 5,330,095 A | 7/1994 | Krude et al. | |
| 5,334,193 A | 8/1994 | Nardella | |
| 5,337,741 A | 8/1994 | Diamond | |
| 5,342,357 A | 8/1994 | Nardella | |
| 5,344,418 A | 9/1994 | Ghaffari | |
| 5,344,433 A | 9/1994 | Talmore | |
| 5,348,554 A | 9/1994 | Imran et al. | |
| 5,366,443 A | 11/1994 | Eggers et al. | |
| 5,370,642 A | 12/1994 | Keller | |
| 5,374,265 A | 12/1994 | Sand | |
| 5,383,874 A | 1/1995 | Jackson et al. | |
| 5,400,791 A | 3/1995 | Schlier et al. | |
| 5,401,272 A | 3/1995 | Perkins | |
| 5,405,368 A | 4/1995 | Eckhouse | |
| 5,423,803 A | 6/1995 | Tankovich et al. | |
| 5,423,807 A | 6/1995 | Milder | 606/20 |
| 5,423,811 A | 6/1995 | Imran et al. | 606/41 |
| 5,437,662 A | 8/1995 | Nardella | 606/40 |
| 5,441,576 A | 8/1995 | Bierschenk et al. | |

| | | | |
|---|---|---|---|
| 5,443,441 A | 8/1995 | De Claviere | |
| 5,445,146 A | 8/1995 | Bellinger | |
| D363,349 S | 10/1995 | Dittert | |
| 5,458,596 A | 10/1995 | Lax et al. | 606/31 |
| 5,462,521 A | 10/1995 | Brucker et al. | 604/20 |
| 5,464,436 A | 11/1995 | Smith | 607/89 |
| 5,474,528 A | 12/1995 | Meserol | |
| 5,484,432 A | 1/1996 | Sand | |
| 5,489,279 A | 2/1996 | Meserol | |
| 5,496,312 A | 3/1996 | Klicek | |
| 5,507,790 A | 4/1996 | Weiss | |
| 5,509,916 A | 4/1996 | Taylor | |
| 5,514,130 A | 5/1996 | Baker | |
| 5,522,814 A | 6/1996 | Bernaz | |
| 5,527,350 A | 6/1996 | Grove et al. | |
| 5,546,214 A | 8/1996 | Black et al. | |
| 5,558,666 A | 9/1996 | Dewey et al. | |
| 5,569,242 A | 10/1996 | Lax et al. | 606/42 |
| 5,584,863 A | 12/1996 | Rauch et al. | |
| 5,595,568 A | 1/1997 | Anderson et al. | |
| 5,609,573 A | 3/1997 | Sandock | |
| 5,618,284 A | 4/1997 | Sand | |
| 5,620,478 A | 4/1997 | Eckhouse | |
| 5,626,631 A | 5/1997 | Eckhouse | |
| 5,647,871 A | 7/1997 | Levine et al. | |
| 5,651,780 A * | 7/1997 | Jackson et al. | 606/1 |
| 5,660,836 A | 8/1997 | Knowlton | |
| 5,672,173 A | 9/1997 | Gough et al. | |
| 5,681,282 A | 10/1997 | Eggers et al. | |
| 5,683,366 A | 11/1997 | Eggers et al. | |
| 5,683,380 A | 11/1997 | Eckhouse et al. | |
| 5,688,267 A | 11/1997 | Panescu et al. | |
| 5,692,058 A | 11/1997 | Eggers et al. | |
| 5,693,045 A | 12/1997 | Eggers | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,697,926 A | 12/1997 | Weaver | |
| 5,702,387 A * | 12/1997 | Arts et al. | 606/45 |
| 5,707,403 A | 1/1998 | Grove et al. | |
| 5,720,772 A | 2/1998 | Eckhouse | |
| 5,723,803 A | 3/1998 | Kurakake | |
| 5,725,565 A | 3/1998 | Smith | |
| 5,728,141 A | 3/1998 | Calbet Benach et al. | |
| 5,735,844 A | 4/1998 | Anderson et al. | |
| 5,735,846 A | 4/1998 | Panescu et al. | |
| 5,755,751 A | 5/1998 | Eckhouse | |
| 5,755,753 A | 5/1998 | Knowlton | 606/33 |
| 5,769,879 A | 6/1998 | Richards et al. | |
| 5,778,894 A | 7/1998 | Dorogi et al. | |
| 5,792,138 A * | 8/1998 | Shipp | 606/38 |
| 5,810,801 A | 9/1998 | Anderson et al. | |
| 5,814,040 A | 9/1998 | Nelson et al. | |
| 5,817,089 A | 10/1998 | Tankovich et al. | |
| 5,817,090 A | 10/1998 | Abergel et al. | |
| 5,820,626 A | 10/1998 | Baumgardner | |
| 5,828,803 A | 10/1998 | Eckhouse | |
| 5,843,078 A | 12/1998 | Sharkey | |
| 5,843,143 A | 12/1998 | Whitehurst | |
| 5,849,029 A | 12/1998 | Eckhouse et al. | |
| 5,871,524 A | 2/1999 | Knowlton | 606/31 |
| 5,885,273 A | 3/1999 | Eckhouse et al. | |
| 5,919,219 A | 7/1999 | Knowlton | 606/33 |
| 5,964,749 A | 10/1999 | Eckhouse et al. | |
| 5,976,123 A | 11/1999 | Baumgardner et al. | |
| 6,007,570 A | 12/1999 | Sharkey et al. | |
| 6,009,876 A | 1/2000 | Yavitz | |
| 6,014,579 A * | 1/2000 | Pomeranz et al. | 600/374 |
| 6,017,354 A * | 1/2000 | Culp et al. | 606/170 |
| 6,030,381 A | 2/2000 | Jones et al. | |
| RE36,634 E | 3/2000 | Ghaffari | |
| 6,047,215 A | 4/2000 | McClure et al. | |
| 6,053,909 A | 4/2000 | Shadduck | |
| 6,053,910 A | 4/2000 | Fleenor | |
| 6,081,749 A | 6/2000 | Ingle et al. | |
| 6,083,221 A | 7/2000 | Fleenor et al. | |
| 6,091,995 A | 7/2000 | Ingle et al. | |
| 6,101,418 A | 8/2000 | Benach | |
| 6,113,593 A | 9/2000 | Tu et al. | |
| 6,159,194 A | 12/2000 | Eggers et al. | |
| 6,165,169 A | 12/2000 | Panescu et al. | |
| 6,171,332 B1 | 1/2001 | Whitehurst | |
| 6,174,325 B1 | 1/2001 | Eckhouse | |
| 6,214,034 B1 | 4/2001 | Azar | |
| 6,216,704 B1 * | 4/2001 | Ingle et al. | 128/898 |
| 6,241,753 B1 | 6/2001 | Knowlton | 607/99 |
| 6,264,652 B1 | 7/2001 | Eggers et al. | |
| 6,277,116 B1 | 8/2001 | Utely et al. | 606/42 |
| 6,280,438 B1 | 8/2001 | Eckhouse et al. | |
| 6,287,305 B1 * | 9/2001 | Heim et al. | 606/41 |
| 6,325,799 B1 | 12/2001 | Goble | |
| 6,381,498 B1 | 4/2002 | Knowlton | |
| 6,405,090 B1 | 6/2002 | Knowlton | |
| 6,413,253 B1 | 7/2002 | Koop et al. | |
| 6,413,255 B1 | 7/2002 | Stern | |
| 6,428,536 B2 | 8/2002 | Panescu et al. | |
| 6,430,446 B1 | 8/2002 | Knowlton | 607/101 |
| 6,438,424 B1 | 8/2002 | Knowlton | |
| 6,453,202 B1 | 9/2002 | Knowlton | |
| 6,454,764 B1 | 9/2002 | Fleenor et al. | |
| 6,461,378 B1 | 10/2002 | Knowlton | 607/104 |
| 6,464,689 B1 | 10/2002 | Qin et al. | |
| 6,470,216 B1 | 10/2002 | Knowlton | 607/101 |
| 6,506,189 B1 * | 1/2003 | Rittman et al. | 606/41 |
| 6,514,243 B1 | 2/2003 | Eckhouse et al. | |
| 6,524,308 B1 | 2/2003 | Muller et al. | |
| 6,533,781 B2 | 3/2003 | Heim et al. | |
| 6,537,272 B2 | 3/2003 | Christopherson et al. | |
| 6,544,258 B2 | 4/2003 | Fleenor et al. | |
| 6,567,262 B2 | 5/2003 | Meir | |
| 6,572,639 B1 | 6/2003 | Ingle et al. | |
| 6,575,969 B1 | 6/2003 | Rittman, III et al. | |
| 6,611,706 B2 | 8/2003 | Avrahami et al. | |
| 6,662,054 B2 | 12/2003 | Kreindel et al. | |
| 6,684,107 B1 | 1/2004 | Binder | |
| 6,690,976 B2 | 2/2004 | Fenn et al. | |
| 6,702,808 B1 * | 3/2004 | Kreindel | 606/9 |
| 6,749,624 B2 | 6/2004 | Knowlton | 607/104 |
| 6,754,895 B1 * | 6/2004 | Bartel et al. | 717/171 |
| 6,981,941 B2 * | 1/2006 | Whitman et al. | 600/1 |
| 6,981,970 B2 | 1/2006 | Kami | |
| 6,997,923 B2 | 2/2006 | Anderson et al. | |
| 7,022,121 B2 | 4/2006 | Stern et al. | |
| 7,108,689 B2 | 9/2006 | Eckhouse et al. | |
| 7,229,436 B2 | 6/2007 | Stern et al. | |
| 2001/0014819 A1 * | 8/2001 | Ingle et al. | 607/99 |
| 2001/0034519 A1 | 10/2001 | Goble et al. | |
| 2003/0187488 A1 | 10/2003 | Kriendel et al. | |
| 2003/0212393 A1 | 11/2003 | Knowlton et al. | |
| 2004/0000316 A1 | 1/2004 | Knowlton et al. | |
| 2004/0002704 A1 | 1/2004 | Knowlton et al. | |
| 2004/0002705 A1 | 1/2004 | Knowlton et al. | |
| 2004/0030332 A1 | 2/2004 | Knowlton et al. | |
| 2004/0034346 A1 | 2/2004 | Stern et al. | |

FOREIGN PATENT DOCUMENTS

| | | |
|---|---|---|
| CN | 1075892 | 9/1993 |
| DE | 1 949 534 | 4/1970 |
| DE | 31 21 683 | 12/1982 |
| DE | 44 00 714 | 7/1995 |
| EP | 0 063 875 | 4/1982 |
| EP | 0091853 | 10/1983 |
| EP | 0 397 178 | 5/1990 |
| EP | 0 395 307 | 10/1990 |

| | | |
|---|---|---|
| EP | 0 519 415 | 12/1992 |
| EP | 0565331 B1 | 10/1993 |
| EP | 0755698 A2 | 1/1997 |
| EP | 0763371 A2 | 3/1997 |
| FR | 2 609 245 | 7/1988 |
| GB | 167667 | 8/1921 |
| JP | 3162870 | 7/1991 |
| JP | 04-89068 | 3/1992 |
| JP | 05-261160 | 10/1993 |
| JP | 6-125993 | 5/1994 |
| JP | 06-285175 | 10/1994 |
| NZ | 266678 | 12/1997 |
| SE | 465953 | 11/1991 |
| WO | 89/00871 | 2/1989 |
| WO | 90/14836 | 12/1990 |
| WO | 91/15264 | 10/1991 |
| WO | 92/05834 | 4/1992 |
| WO | 92/19414 | 11/1992 |
| WO | 93/13816 | 7/1993 |
| WO | 94/26228 | 11/1994 |
| WO | 96/27240 | 9/1996 |
| WO | 96/27327 | 9/1996 |
| WO | 96/32051 | 10/1996 |
| WO | 96/34568 | 11/1996 |
| WO | 96/39914 | 12/1996 |
| WO | 97/18765 | 5/1997 |
| WO | 97/18768 | 5/1997 |
| WO | 97/24992 | 7/1997 |
| WO | 98/03117 | 1/1998 |
| WO | 98/03220 | 1/1998 |
| WO | 98/52645 | 11/1998 |
| WO | WO 99/16502 | 4/1999 |
| WO | 03024524 | 3/2003 |
| WO | 03/068310 A2 | 8/2003 |
| WO | 2004/087253 A2 | 10/2004 |

OTHER PUBLICATIONS

Kincade, K., *Demand for Laser Resurfacing Soars: Quicker Healing, Less Risk of Scarring*, Dermatology Times, 1995; 16(10).

Fitzpatrick, R., *Treatment of Wrinkles with the UltraPulse CO2 Laser*, Laser Aesthetics, Inc., The Cool Touch Laser Brochure (date unknown).

Laser Aesthetics, Inc., *Cool Touch Model 130 Technical Specifications*, Brochure (date unknown).

National Health Communications, Inc., *New Laser Eliminates 'Lipstick Bleed'*, Press Release, Jul. 1993.

Danielson, C. , *Age-Related Thermal Stability and Susceptibility to Proteolysis of a Rat Bone Collagen . . .* , Chem, Great Britain, pp. 697-701 (1990).

Houghton Mifflin Co., *American Heritage Dictionary*, p. 309 (1976).

Danielson, C., *Thermal Stability of Reconstituted Collagin Fibrils, Shrinkage Characteristics upon In Vitro Maturation*, Mechanisms of Aging and Development, vol. 15, pp. 269-278 (1981).

Kronick et al., *The Locations of Collagens with Different Thermal Stabilities in Fibrils of Bovine Recticular Dermis*, Connective Tissue Research, vol. 18, pp. 123-124 (1988).

Mainster, M.A., *Ophthalmic Applications of Infrared Lasers—Thermal Considerations*, Visual Sci., pp. 414-420 (Apr. 1979).

Pearce, et al., *Kinetic Models of Laser-Tissue Fusion Processes*, ISA, Paper #93-044, pp. 355-360 (1993).

Adrian, R.M., *Treatment of Facial Telangieclasia Using the VersaPulse Variable Pulse Width Frequency Doubled Neodymium, YAG Laser: A Case Report*, date unknown.

Chess, C. and Chess, Q., *Cool Laser OPtics Treatment of Large Telangiestasia of the Lower Extremities*, J. Dermatol Surg. Oncol. 1993; 19:74-80.

Coulson, W.F. et al., *Nanablative Laser Treatment of Facial Rhytides: Animal Study*, Abstract for BiOs '98 Symposium Conference: bo-05—Cutaneous Applications of Lasers, Jan. 24-30, 1998, San Jose, CA.

Ghersetich, et al., "Ultrastructural Study of Hyaluronic Acid Before and After the Use of a Pulsed Electromagnetic Field, Electrorydesis, in the Treatment of Wrinkles", International Journal of Dermatology, vol. 33, No. 9, Sep. 1994, pp. 661-663.

Federal Register 54(78) (1989) 17710-17801.

Ranganathan R, "Promises for ultrasonic waves on activity of silica gel and some supported catalyst," Ind Eng Chem Prod Res Develop. (1973) 12(2):155-158.

Rasmussen D, "Isotonic and isometric thermal contraction of human dermis: I. Technique and controlled study," J Invest Dermatol. (1964) 43:333-339.

Rassing J, "Measurement of ultrasonic absorption in a gel by light diffusion and resonator method," J Molec Liq. (1983) 26:97-108.

Rastegar S, "Technique for measurement of one-dimensional instantaneous ablative velocity,"Lasers Surg Med. (1988) 8:533-535.

Raulin C, "Treatment of a nonresponding port-wine stain with a new pulsed light-source (Photoderm VL)," Surg Med. (1997) 21:203-208.

Raulin C, "Treatment of benign venous malformation with an istense pulsed light source (Photoderm VL)," Eur J Dermatol. (1997) 7:279-282.

Raulin C, "Treatment of essential telangiectasias with an intense pulsed light source (Photoderm VL),"Dermatol Surg. (1997) 23:941-946.

Raulin C, "Treatment of port-wine stains with a noncoherent pulsed light source," Arch Dermatol. (1999) 135:679-683.

Raulin C, "Treatment of venous malformations with an intense pulsed light source (IPLS) technology: a retrospective study," Lasers Surg Med. (1999) 25:170-177.

Reddy GK, "Biochemistry and biomechanics of healing tendon: part 2. Effects of combined laser therapy and electrical stimulation," Med Sci Sports Ex. (1998) 30(6):794-800.

Reddy GK, "Laser Photostimulation of collagen production in healing rabbit tendons," Lasers Surg Med. (1998) 22:281-287.

Reyes BA, "Treatment of port-wine stains during childhood with the flashlamp-pumped pulsed dye laser," J Am Acad Dermatol. (1990) 23:1142-1148.

Rink JD, "Cellular characterization of adipose tissue from various body sites of a female, " J Clin Endocr Metabol. (1996) 81(7):2443-2447.

Rohrich RJ, "Comparative lipoplasty analysis of in vivo-treated adipose tissue," Cosmetic. (2000) 105(6):2152-2158.

Rosenbaum M, "An exploratory investigation of the morphology and biochemistry of cellulite," Cosmetic. (1998) 101 (7): 1934-1939.

Ross EV, "Effects of CO2 laser pulse duration in ablative and residual thermal damage: implications for skin resurfacing," Lasers Surg Med. (1996) 19:123-129.

Rowe RW, "Photodynamic therapy begins to shine," The Lancet. (1998) 351:1496.

Ruiz-Esparza J, "The medical face lift: a noninvasive, nonsurgical approach to tissue tightening in facial skin using nonablative radiofrequency," Dermatol Surg. (2003) 29:325-332.

Rulz-Esparza J, "Selective melanothermolysis: a histological study of the candela 510 nm pulsed dye laser for pigmented lesions," Am S Laser Med Surg, (1992) Abstr322.

Sacknell EJ, "Lasers in urology," Am S Laser Med Surg, (1991) Abstr252.

Sadick NS, "A dual wavelength approach for laser/intense pulsed light source treatment of lower extremity veins," J Am Acad Dermatol. (2002) 46:66-72.

Sadick NS, "A structural approach to nonablative rejuvenation," Cosmet Dermatol. (2002) 15(12):39-43.

Sadick NS, "Advances in laser surgery for leg veins: bimodal wavelength approach to lower extremity vessels, new cooling techniques, and longer pulse duration," Dermatol Surg. (2002) 28: 16-20.

Sadick NS, "Long-term photoepilation using a broad-spectrum intense pulsed light source," Arch Dermatol. (2000) 136:1336-1340.

Sanchez Burson JL, "Gel de transmision de ultrasonidos: estudio comparativo de deistintas formulaciones," Farm Hosp. (1991) 15(6):394-399.

Sapijaszko MJA, "Er: YAG laser skin resurfacing," Dermatologic Clinics. (2002) 20(1):87-95.

Schroeter CA, "intense light source," Dermatol Surg. (1998) 24:743-748.

Schroeter CA, "Clinical significance of an intense, pulsed light source on leg telangiectasias of up to 1mm diameter," Eur J Dermatol. (1997) 7:38-42.

Schroeter CA, "Photoderm VL treatment of leg telangiectasia," J Eu Acad Dermatol Venereol. (1995) 5(1): AbstrW76.

Schwiner SR, "The effect of ultrasound coupling gels on sperm motility in vitro," Fertil Steril. (1984) 42(6):946-947.

Selli C, "Transurethral radiofrequency thermal ablation of prostatic tissue: a feasibility study in humans," Urology. (2001) 57:78-82.

Sheean LA, "Arrest of embryo development by ultrasound coupling gel," Fertil Steril. (1986) 45(4):568-571.

Skinner SM, "A preliminary study of the effects of laser radiation on collagen metabolism in cell culture," Austr Dental J. (1996) 41(3):188-192.

Smith T, "532 nm green laser beam treatment of superficial varicosities of the lower extremities," Lasers Surg Med. (1988) 8: 130-134.

Steiger E, "Comparison of different pulsed and Q-switched solid state laser systems for endoscopic laser induced shock wave lithotripsy: performance and laser/stone interaction," In: Laser surgery: advanced characterization, therapeutics, and systems, II, Ed. Joffe SN (1990) 94-101, SPIE Press.

Stenn KS, "Controls of hair follicle cycling," Physiol Rev. (2001) 81(1):449-494.

Strickland BE, "A 5kV, 250kA rep-rated pulser using parallel ignitrons," In: 7th Pulsed Power Conference. (1989) 728-731.

Sunde, D, "Traumatic tattoo removal: comparison of four treatment methods in an animal model with correlation to clinical experiments," Lasers Surg Med. (1990) 10:158-164.

Sunn JY, "A new approach to the treatment of hemagiomas," Am S Laser Med Surg, (1991) Abstr263.

Suthamjariya K, "Chapter 40: Lasers in dermatology," In: Biomedical Photonics Handbook, Ed. Vo-Dinh T (2002) CRC Press:Boca Raton.

Svaasand LD, "Light and drug distribution with topically administered photosensitizers," Lasers Med Sci. (1996) 11:261-265.

Szeimies RM, "A possible new incoherent lamp for photodynamic treatment of superficial skin lesions," Acta Derm Venercol. (1994) 74:117-119.

Tan OT, "Action spectrum of vascular specific injury using pulsed irradiation," J Invest Dermatol. (1989) 92:868-871.

Tan OT, "EMLA for laser treatment of port-wine stains in children," Laser Surg Med. (1992) 12:543-548.

"Acne Phototherapy: breaking the barriers in acne clearance," (2002) http://www.radiancy.com/department/?did=17.

"Photoepilation: hair removal in a whole new light," (2002) http://www.radiancy.com/article/?id=03c0e2b38f15b4d833e86c99d85279a1.

Achauer BM, "Argon laser treatment of telangiectasia of the face and neck: 5 years experience," Lasers Surg Med. (1987) 7:495-498.

Alora MBT, "Recent developments in cutanous lasers," Lasers Surg Med. (2000) 26: 108-118.

Alster TS, "Treatment of port-wine stains of the flashlamp-pumped pulsed dye laser: extended clinical experiments in children and adults," Annals Plast Surg. (1994) 32(5):478-484.

Altshuter GB, "Extended theory of selective photothermolysis," Lasers Surg Med. (2001) 29:416-432.

Anavari B, "Selective cooling of biological tissues: applications for thermal mediated therapeutic procedures," Phys Med Biol. (1995) 40:241-252.

Anderson RR, "Mechanics of selective vascular changes caused bu dye lasers," Lasers Surg Med. (1983) 3:211-215.

Anderson RR, "Microvasculature can be selectively damages using dye lasers: a basic theory and experimental evidence in human skin," Lasers Surg Med. (1981) 1:263-276.

Anderson RR, "Selective photothermolysis: precise microsurgery by selective absorption of pulsed radiation," Science. (1983) 220:524-527.

Anderson TF, "Chapter 3: light sources in photomedicine," In: Clinical photomedicine, Ed. Lim HW (1993) 37-58, Marcel Dekker:New York Angermier MC, "Treatment of facial vascular lesions with intense pulsed light," J Cutan Laser Ther. (1999) 1:95-100.

Apfelberg DA, "Preliminary investigation of KTP/532 laser light in the treatment of hemangiomas and tattoos," Lasers Surg Med. (1986) 6:38-42.

Apfelberg DBA, "Dot or pointillistic method for improvement in results of hypertrophic scarring in the Ar laser treatment of port wine hemangiomas," Lasers Surg Med. (1987) 6:552-558.

Apfelberg DBA, "Intralesional laser photocoagulation: steroids as a adjunct to surgery for massive hemangiomas and vascular malformations," Ann Plast Surg. (1987) 35:144-149.

Apfelberg DBA, "Progress report on extended use of the Argon laser for cutaneous lesions," Lasers Surg Med. (1980) 1:71-83.

Apfelberg DBA, "Results of argon and CO2 laser experiments on telangiectasia of the lower extremity: a preliminary report," Lasers Surg Med. (1983) Abstr165.

Apfelberg DBA, "Study of three laser systems for treatment of superficial varicosities of the lower extremity," Lasers Surg Med. (1987) 7:219-223.

Apfelberg DBA, "Superpulse CO2 laser treatment of facial syringomata," Lasers Surg Med. (1987) 7:533-537.

Apfelberg DBA, "Update on laser usage in treatment of decortive tattoo," Lasers Surg Med. (1982) 2:169-177.

Appelberg DBA, "Progress report on multicenter study of laser-assisted lipsuction," Aesth Plast Surg. (1994) 8:259-264.

Ara G, "Irradiation of pigmented melanoma cells with high intensity pulsed radiation that generates acoustic waves and kills cells," Lasers Surg Med. (1990) 10:52-59.

Arner P, "Adrenergic receptor function in fat cells," Am J Clin Nutr. (1992) 55:228S-236S.

Arnoczky SP, "Thermal modification of connective tissues: basic science considerations and clinical implications," J Am Acad Orthop Surg. (2000) 8(5):305-313.

Ashinoff R, "Flashlamp-pumped pulsed dye laser for port wine stains in infancy: earlier versus later treatment," J Am Acad Dermatol. (1991) 24:467-472.

Ashinoff R, "Q-switched ruby laser treatment of benign epidermal pigmented lesions," Am S Laser Med Surg, (1992) Abstr325.

Babbs CF, "Equipment for local hyperthermia therapy of cancer," Med Instr. (1982) 16(5):245-248.

Beacco, C, "Mathematical modeling coagulation," Am S Laser Med Surg. (1992):Abstr1.

Bell T, "100 msec pulsed CO2 laser resurfacing of lower eyelids: erythemia and rhytides reduction," In: Lasers in Surgery: Advanced Characterization, Therapeutics, and Systems VII, Ed. Anderson RR (1997) 360-366, SPIE Press.

Bjerring P, "Selective non-ablative wrinkle reduction by laser," J Cutan Laser Ther. (2000) 2:9-15.

Jacques SL, "The role of skin optics in diagnostics and therapeutics uses of lasers," In: Lasers in Dermatology, Ed. Setiner R (1991) 1-21, Springer-Verlag:Berlin.

Jaitly NC, "MV long pulse generator with low ripple and low droop," In: 8th International Pulsed Power Conference, Ed. White R (1991) 161-165, IEEE.

Jaitly NC, "Design and testing of a multi-output 300kV prototype induction cell pulsed power supply for DARHT," In: 10th Int'l Pulsed Power Conference, (1995) 1412-1421, IEEE.

Jay HH, "Victory over veins," NYT. (1996) Jul. 21.

Johannigmann J, "Ein neues ultraschall-kontaktgel," Geburtsh u. Frauenheilk. (1974) 34:12.

Johnson F, "Intense pulsed light treatment of hirsutism: case reports of skin phototypes V and VI," J Cutan Laser Ther. (1999) 1:233-237.

Johnston M, "Spectrophotometric and laser doppler evaluation of normal skin and port wine stains treated with argon laser," Lasers Surg Med. (1983) Abstr166.

Jordan R, "Laser resurfacing of the skin for the improvement of facial acne scarring," In: Midwest Midlands Development and Evaluation Committee Report. (Nov. 1998).

Jost G, "Experience with collagen injection for the correction of contour deficiencies," Aesth Plast Surg. (1985) 9:163-165.

Kalka K, "Photodynamic therapy in dermatology," J Am Acad Dermatol. (2000):389-413.

Kaminester LH, "Suntanning centers," JAMA. (1980) 244(11):1258-1259.

Kaufmann R, "Pulsed 2*94-mm erbium-YAG laser skin ablation—experimental results and first clinical application," Clin Exp Dermatol. (1990) 15:389-393.

Keljzer M, "Laser beam diameter diameter for port wine stain treatment," Lasers Surg Med. (1991) 11:601-605.

Kennedy JC, "Photodynamic therapy with endogenous protoporphyrin IX: basic principles and present clinical experiences," J Photochem Photobiol B: Biol. (1990) 6:143-148.

Kilmer SL, "Pulsed dye laser treatment of rhytids," Am S Laser Med Surg, (1997) Abstr194.

Kim D, "Role of dermal melanocytes in cutaneous pigmentation of stasis dermatitis," J Korean Med Sci. (2002) 17:648-654.

Kincade K, "Demand for laser resurfacing soar: quicker healing, less risk of scarring," Dermatol Times. (1995) 16 (10):1966-1967.

Koch RJ, "Initial experience with the NovaScan™ CO2 Laser Handpiece," Am S Laser Med Surg, (1997) Abstr196.

Koechner W, Solid state laser engineering, Ed. MacAdam DL (1976) Springer-Verlag:New York.

Kolobov VI, "The anomalous skin effect in gas discharge plasmas," Plasma Sources Sci Technol. (1997) 6:R1-R17.

Lakmaker O, "Modeling the color perception of port wine stains and its relation to the depth of laser coagulation blood vessels," Lasers Surg Med. (1993) 13:219-226.

Lask G, "Laser skin resurfacing with the Silk Touch Flashscanner for facial rhytides," Dermatol Surg. (1995) 21:1021-1024.

Lask G, "Nonablative laser treatment of facial rhytides," In: Lasers-in Surgery: Advanced Characterization, Therapeutics, and Systems VII, Ed. Anderson RR (1997) 338-349, SPIE Press.

Leveen HH, "Tumor eradication by radiofrqeuency therapy," JAMA. (1976) 235(20):2198-2200.

Levine D, "Effects of 33-MHz ultrasound on caudal thigh muscle temperature in dogs," Veterin Surg. (2001) 30:170-174.

Levins PC, "Q-switched ruby laser treatment of tattoos," Am S Laser Med Surg, (1991) Abstr255.

Ley A, "Capacitive electric transfer (CET), non-invasive deep hyperthermia technique in the treatment of cerebral gliomas, preliminary results," Neurocinguia. (1992) 3:118-123.

Lopez MJ, "The effect of radiofrequency energy on the ultrastructure of joint capsular collagen," J Arthro Rel Surg. (1998) 14(5):495-501.

Lowe NJ, "Skin resurfacing with the ultrapulse carbon dioxide laser," Dermatol Surg. (1995) 21:1025-1029.

Magee TR, "Vein marking through ultrasound coupling gel," Eur J Vasc Surg. (1990) 4:491-492.

Majaron B, "Deep coagulation of dermal collagen with repetition Er:YAG laser," Lasers Surg Med. (2000) 26:215-222.

Majaron B, "Er:YAG laser skin resurfacing using repetition long-pulse experiment and cryogen spray cooling: I: histological study," Lasers Surg Med. (2001) 28:121-130.

Majaron B, "Er:YAG laser skin resurfacing using repetition long-pulse experiment and cryogen spray cooling: II: theoretical analysis," Lasers Surg Med. (2001) 28:131-137.

Manstein D, "Effects of fluence and pulse duration for flashlamp exposure on hair follicles," In: 21st Ann Mtg Am Soc Laser Med Surg. (2001): 1-18.

Margolis RJ, "Visible action spectrum for melanin-specific select photothermolysis," Lasers Surg Med. (1989) 9:389-397.

Marhic ME, "White-light flashlamp-pumped dye laser for photography through endoscopes," Optics Comm. (1983) 45(1):21-25.

Mascaro JM, "Subacute cutaneous lupus erythematosus," J Eu Acad Dermatol Venereol. (1995) 5(1):AbstrW79.

Matsukawa T, "Comparison of infrared thermometer with thermocouple for monitoring skin temperature," Cnt Care Med. (2000) 28(2):532-6.

McCaughen JS, "Chapter 21: Photodynamic therapy: an 8-year experience," In: Photodynamic therapy: basic principles and clinical applications, Ed. Henderson BW (1992) 323-331, Marcel Dekker:New York.

McCaughen JS, "Photodynamic therapy for cutaneous and subcutaneous malignant neoplasms," Arch Surg. (1989) 124:211-216.

McClurken M, "Collagen shrinkage and vessel sealing." In: Technical Brief #300, (2001) TissueLink, Dover, NH.

McMeekin TO, "Comparison of Q-switched ruby, pigmented lesion dye laser and copper vapor laser treatment of benign pigmented lesions of the skin," Am S Laser Med Surg, (1992) Abstr327.

Garden JM, "Effect of dye laser pulse duration on selective cutaneous vascular injury," J Invest Dermatol. (1986) 87:653-657.

Garden JM, "The treatment of port-wine stains by the pulsed dye laser: analysis of pulse duration and long-term therapy," Arch Dermatol. (1988) 124:889-896.

Geddes LA, "The specific resistance of biological materials: a compendium of data for the biomedical engineer and physiologist," Med Biol Eng. (1967) 5:271-293.

Geronamus RG, "Q-switched ruby laser therapy of nevus of OTA," Am S Laser Med Surg, (1992) Abstr329.

Geronemus RG, "The medical necessity of evaluation and treatment of port-wine stains," J Dermatol Surg Oncol. (1991) 17:76-79.

Ghersetich I, "Ultrastructural study of Hyaluronic acid and after the use of a pulsed electromagnetic field, electrorydesis, in the treatment of wrinkles," Int'l J Dermatol. (1994) 33(9):661-663.

Gijsbers GHM, "CW laser ablation velocities as a function of absorption in experimental 1-D tissue model," Lasers Surg Med. (1991) 11:287-296.

Gijsbers GHM, "Effect of force on ablation depth for a XeCl excimer laser beam delivered by an optical fiber in contact with arterial tissue under saline," Lasers Surg Med. (1992) 12:576-584.

Gold MH, "One-year follow-up using an intense pulsed light source for long-term hair removal," J Cutan Laser Ther. (1999) 1:167-171.

Goldberg DJ, "Benign pigmented lesions of the skin: treatment with Q-switched ruby, copper vapor, and pigmented lesions laser," Am S Laser Med Surg, (1992) Abstr328.

Goldberg DJ, "Erbium:YAG laser resurfacing: what is the role?" Aesth Surg J. (1998) 18(4):255-260.

Goldberg DJ, "New collagen formation after dermal remodeling with an intense pulsed light source," J Cutan Laser Ther. (2000) 2:59-61.

Goldberg DJ, "Nonablative treatment of rhytides with intense pulsed light," Lasers Surg Med. (2000) 26(2):196-200.

Goldberg DJ, "Q-switched Nd:YAG laser: rhytides improvement by non-ablative dermal remolding," J Cutan Laser Ther. (2000) 2:157-160.

Goldberg DJ, "Q-switched ruby laser treatment of benign pigmented lesions: the New Jersey experience," Am S Laser Med Surg, (1991) Abstr260.

Goldman L, "600 nm flash pumped dye laser for fragile telangiectasia of the elderly," Lasers Surg Med. (1993) 13:227-233.

Goldman MP, "Chapter 17: Sclerotherapy treatment for varicose and telangiectatic leg veins," In: Cosmetic Surgery of the Skin: Principles and Techniques, (1997) 256-271, Mosby:St. Louis.

Goldman MP, "Chapter 2: Treatment of cutaneous vascular lesions," In: Cutaneous Laser Surgery, Ed. Goldman MP (1994) 19-105, Mosby:St. Louis.

Goldman MP, "Photothermal sclerosis of leg veins," Dermatol Surg. (1996) 22:323-330.

Goldman MP, "Pulsed dye laser treatment of telangietases with and without subtherapeutic sclerotherapy," J Am Acad Deramtol. (1990) 23:23-30.

Goldman MP, "Treatment of port-wine stains (capillary malformation) with the flashlamp-pumped pulsed dye laser," J Pediatr. (1993) 122:71-77.

Goldman MP, "Laser and noncoherent pulsed light treatment of leg telangiectasias and venules," Cosmet Dermatol. (1995) 8(10):43-44.

Gomer H, "Military laser burns away skin flaws," The Sunday Times (1995) Oct. 15:§6.10.

Gonzalez E, "Treatment of telangiectases and other benign vascular lesions with the 577nm pulsed dye laser," J Am Acad Dermatol. (1992) 27:220-226.

Inui S, "Androgen-inducible TGF-b1 from balding dermal papilla cells inhibits epithelial cell growth: a clue to understanding paradoxical effects of androgen on human hair growth," FASEB J. (2002) 16(14):1967-1969.

Goudsmit G, "Give cellulite another look," Aesth Med (Date unknown): 34.

Greenway FL, "Regional fat loss from the thigh in obese women after adrenergic modulation," Clin Therapeutics. (1987) 9(6):663-669.

Gregory KW, "Effect of blood upon the selective ablation of atherosclerotic plaque with a pulsed dye laser," Lasers Surg Med. (1990) 10:533-543.

Grema H, "Skin rejuvenation durch nichtablative laser und lichtsysteme: literaturrecherche und ubersicht," Hautarzt. (2002) 53:385-392.

Grevelink JM, "Update on the treatment of benign pigmented lesions with the Q-switched ruby laser," Am S Laser Med Surg, (1992) Abstr326.

Griffiths C, "Restoration of collagen formation in photodamages human skin by tretinoin (retinoic acid)," NEJM. (1993) 329(8):530-535.

Grimes PE, "Laser resurfacing-induced hypopigmentation: histological alternative and repigmentation with topical photochemotherapy," Dermatol Surg. (2001) 27:515-520.

Groot DW, "Comparison of the infrared coagulator and the carbon dioxide laser in the removal of decorative tattoos," J Am Acad Dermatol. (1986) 15:518-522.

Groves N, "Radiofrequency device offers advantages of its own: nonablative technology delivers high amount of deeper, focused energy," Dermatol Times. (2002) 23(7).

Hanson An, "Quantitation of type I to type III collagen ratios in small samples of human tendon, blood vessels, and atherosclerotic plaque," Anal Biochem. (1983) 130:32-40.

Haustein UF, "Clinical features, diagnosis, and treatment of cutaneous lupus erythematosus," J Eu Acad Dermatol Venereol. (1995) 5(1):AbstrW77.

Hayashi K, "The effect of nonablative laser energy on the ultrastructure of joint capsular collagen," Arthroscopy. (1996) 12(4):474-481.

Higuchi Y, "Exposure of the dorsal root ganglion in rats to pulsed radiofrequency currents activates dorsal horn lamina I and II neurons," Neurosurg. (2002) 50(4):850-856.

Hinderer UT, "Dermal and subdermal tissue filling with fetal connective tissue and cartilage, collagen and silicon," Aesth Plast Surg. (1990) 14:239-248.

Hulsbergen Henning JP, "Clinical and histological evaluation of port wine stain treatment with a microsecond-pulsed dye laser at 577 nm," Lasers Surg Med. (1984) 4:375-380.

Hulsbergen Henning JP, "Port wine stain coagulation experiment with a 540 nm continuous wave dye-laser," Lasers Surg Med. (1983) 2:205-210.

Hulsbergen Henning JP, "Rhinophyma treatment by Ar laser," Lasers Surg Med. (1983) 2:211-215.

Hulsbergen Henning JP, "Treatment of keloids and hypertrofic scars with an Ar laser," Lasers Surg Med. (1986) 6:72-75.

Bracco D, "Segmental body composition assessed by bioelectrical impedance analysis and DEXA in humans," J Appl Physiol. (1996) 81(6):2580-2587.

Brauner GJ, "Treatment of pigmented lesions with the flashlamp pumped PLDL ("brown spot") laser," Am S Laser Med Surg, (1992) Abstr324.

Bray GA, "Current and potential drugs for treatment of obesity," Endocr Rev. (1999) 20(6):805-875.

Broska P, "Comparison of the argon tunable dye laser with the flashlamp pulsed dye laser in the treatment of facial telangietasia," J Dermatol Surg Oncol. (1994) 20:749-753.

Brugmans MJP, "Temperature response of biological materials to pulsed non-ablative CO2 laser irradiation," Lasers Surg Med. (1991) 11:587-594.

Burke KE, "Bovine collagen implant: histologic chronology in pig dermis," J Dermatol Surg Oncol. (1983) 9:889-895.

Cates MC, "A long pulse (5µs) e-beam pumped XeF laser," In: High-power gas lasers, Ed. Avizonis PV (1990) 34-43, SPIE Press.

Cates MC, "Excimer laser produced plasma studies," In: Laser-assisted processing II, Ed. Laude LD (1990) 102-111, SPIE Press.

Ceronamus RG, "Use of the Q-switched ruby laser to treat tattoos and benign pigmented lesions of the skin," Am S Laser Med Surg, (1991) Abstr259.

Chen S, "Effects of all-trans retinoic acid on UVB-irradiated and non-irradiated hairless mouse skin," J Invest Dermatol. (1992) 98:248-254.

Chess C, "Cool laser optics treatment of large telangiectasia of the lower extremities," J Dermatol Surg Oncol. (1993) 19:74-80.

Cheung Ay, "Deep local hyperthermia for cancer therapy: external electromagnetic and ultrasound techniques," Cancer Res. (1984) 44:4736S-4744S.

Chissler P, "Tanning beds are not without drawbacks," FDA Consumer. (1983-84) Dec.-Jan. 21-22.

Cliff S, "Treatment of mature port wine stains with the photoderm VL," J Cutan Laser Ther. (1999) 1:101-104.

Colaiuda S, "Treatment of deep underlying reticular veins by Nd:Yag laser and IPL source," Minerva Cardioangiol. (2000) 48:1-6.

Cole-Beuglet C, "Ultrasound mammography for the augmented breast," Radiol. (1983) 146:737-742.

Colver GB, "Port wine stains," J Royal Soc Med. (1987) 80:603.

Colver GB, "Precise dermal damage with an infrared coagulator," Brit J Dermatol. (1986) 114:603-608.

Colver GB, "Tattoo removal using infra-red coagulation," Brit J Dermatol. (1985) 112:481-485.

Colver GB, "The infrared coagulator in dermatology," Dermatol Ther. (1989) 7(1):155-167.

Cooper DA, "The domestic pig as a model for evaluating Olestra's nutritional effects," J Nutr. (1997) 127:1555S-1565S.

Daniell MD, "A history of photodynamic therapy," Aust NZ J Surg. (1991) 61:340-348.

Decoste SD, "Comparison of Q-switched ruby and Q-switched Nd:YAG laser treatment of tattoos," Am S Laser Med Surg, (1991) Abstr258.

Devore DP, "Effectiveness of injectable filler materials for smoothing wrinkle lines and depressed scars," Med Prog Tech. (1994) 20:243-250.

Dinehart SM, "Beam profile of the flashlamp pumped pulsed dye laser: support for overlap of exposure spots," Lasers Surg Med. (1994) 15:277-280.

Dover JS, "The role of lasers and light sources in the treatment of leg veins," Dermatol Surg. (1999) 25:328-336.

Dzubow LM, "Leg veins and stretch marks: have they seen the light?" Dermatol Surg. (1996) 22:Abstr321.

Efthymiopoulos T, "High-energy short pulse flashlamps: operation characteristics," Applied Opt. (1977) 16 (1):70-75.

Eli C, "Laser lithotripsy of gallstones by means of a pulsed neodymium-YAG laser: in vitro and animal experiments," Endoscopy. (1986) 18:92-94.

Elman M, "Evaluating pulsed light and heat energy in acne clearance," Radiancy. Jun. 1-4, 2002.

Engelhardt R, "Spectroscopy during laser induced shock wave lithotripsy," In: Laser medical systems engineering, Ed. (1988) 200-204, SPIE Press.

Epstein EH, "Human skin collagen," J Biol Chem. (1978) 253:1336-1337.

Fitzpatrick RE, "Advances in carbon dioxide laser surgery," Clin Dermatol. (1995) 13:35-47.

Fitzpatrick RE, "Flashlamp-pumped pulsed dye laser treatment of port-wine stains," J Dermatol Surg Oncol. (1994) 20:743-748.

Fitzpatrick RE, "Treatment of benign cutaneous pigmented lesions with the candela 510 nm pulsed laser," Am S Laser Med Surg, (1992) Abstr323.

Fitzpatrick RE, "Treatment of leg veins: a comparison of laser therapy with noncoherent, multiwave light sources," In: Lasers and Electro-Optics Society Ann Mtg (LEOS '93), (1993) 238-239, IEEE.

Flock ST, "Er:YAG laser-induced changes in skin in vivo and transfermal drug delivery," In: Lasers in Surgery: Advanced Characterization, Therapeutics, and Systems VII, Ed. Anderson RR (1997) 374-379, SPIE Press.

Flock ST, "Thermal damage of blood vessels in a rat skin-flap window chamber using indocyanio green and a pulsed alexandrite laser: a feasibility study," Lasers Surg Med. (1993) 8:185-196.

Foley PA, "Recent advances: dermatology," BMJ. (2000) 320:850-853.

Foster TD, "The successful use of a photoderm VL in the treatment of a cavernous hemangioma in a dark-skinned infant," Min Inv Surg Nursing. (1996) 20(2):102-104.

Gabriel C. "The dielectric properties of biological tissues: I. Literature survey," Phys Med Biol. (1996) 41:2231-2249.

Garaulet M, "Site-specific difference in the fatty acid comparison of abdominal adipose tissue in an obese population from a Mediterranean area: relative with dietary fatty acids, plasma lipid profile, serum insulin, and central obesity," Am J Clin Nutr. (2001) 74:585-591.

Tan OT, "Histologic response of port-wine stains treatment by argon, carbon dioxide, and tunable dye lasers," Arch Dermatol. (1986) 122:1016-1022.

Tan OT, "Pulsed dye laser treatment of recalcitrant verrucae," Lasers Surg Med. (1993) 13:127-137.

Tan OT, "Treatment of children with port-wine stains using the flashlamp-pulsed tunable dye laser," NEJM. (1989) 320:416-421.

Taylor CR, "Q-switched ruby laser (QRSL) irradiation of benign pigmented lesions: dermal vs epidemal," Am S Laser Med Surg, (1991) Abstr262.

Templeton JL, "Comparison of infrared coagulation and ligation for first and second degree haemorrhoids: a randomized prospective clinical trial," Brit Med J. (1983) 286:1387-1389.

Taner JM, "Laser angioplastic state of the art," Am S Laser Med Surg, (1991) Abstr253.

Thomas EL, "Magnetic resonance imaging of total body fat," J App Physiol. (1998) 85(5):1778-1785.

Tolleth H, "Long-term efficacy of collagen," Aesth Plast Surg. (1985) 9:155-158.

Troccoli J, "Multiple-pulse photocoagulation of blood vessels with a 585nm tunable dye laser," Am S Laser Med Surg. (1992):Abstr2.

Trucco T, "Can electrical charges really stop wrinkles?," NYT. Aug. 17, 1991.

Tunnell JW, "Mathematical model of non-ablative RF heating of skin," 22nd Ann Mtg Am S Laser Med Surg. (2002): Abstr318.

Van Gemert MJC, "Chapter 5: Laser applications in medicine and biology: Can physical modeling lead to an optimized laser treatment strategy for port wine stains," In: Laser applications in medicine and biology, Ed. Wolbarsht ML (1991) 199-276, Plenum Press:New York.

Van Gemert MJC, "In there an optimal laser treatment for port wine stains," Lasers Surg Med. (1986) 6:76-83.

Van Gemert MJC, "Wavelengths for laser treatment of port wine stains for telangiectasia," Lasers Surg Med. (1995) 16:147-155.

Venning VA, "Tattoo removal using infrared coagulation: a dose comparison," Brit J Dermatol. (1987) 117:99-105.

Wagner P, "Percuagine-gel et ultrasonotherapie en pathologie traumatique dusport," La Revue de Medecine. (1982) 32:1681-1683.

Wahrenberg H, "Mechanisms underlying regional differences in lipolysis in human adipose tissue," J Clin Invest. (1989) 14:458-467.

Wajchenberg BL, "Subcutaneous and visceral adipose tissue: their relation to the metabolic syndrome," Endocrine Rev. (2000) 21(6):697-738.

Waldorf HA, "Skin resurfacing of fine to deep rhytides using a char-free carbon dioxide laser in 47 patients," Dermatol Surg. (1995) 21:940-946.

Walls MS, "Thermal modification of collagen," J Shoulder Elbow Surg. (1999) 8:339-344.

Walsh JT, Jr., "Er:YAG laser ablation of tissue: effect of pulse duration and tissue type on thermal damage," Lasers Surg Med. (1989) 9:314-326.

Walsh JT, Jr., "Er:YAG laser ablation of tissue: measurement of ablative rates," Lasers Surg Med. (1989) 9:327-337.

Walsh JT, Jr., "Pulsed CO2 laser tissue ablation: effect of tissue type and pulse duration on thermal damage," Lasers Surg Med. (1988) 8:108-118.

Walsh JT, JR., Pulsed laser ablation of tissue: analysis of the removal process and tissue healing, (1988) Doctoral Thesis, Massachusetts Institute of Technology:Cambridge.

Weiss RA, "Controlled radiofrequency endovenous occlusion using a unique radiofrequency catheter under duplex guidance to eliminate saphenous varicose vein reflux: a 2-year follow-up," Dermatol Surg. (2002) 28(1):38-42.

Weiss RA, "Rejuvenation of photoaged skin: 5 years results with intense pulsed light of the face, neck, and chest," Dermatol Surg. (2002) 28:1115-1119.

Weiss RA, "Treatment of Poikilderma of civatte with an intense pulsed light source," Dermatol Surg. (2000) 26:823-828.

Welch AJ, "Practical models for light distribution in laser tissue," Lasers Surg Med. (1987) 6:488-493.

Werner JA, "Die Hamangiombehandlund mit dem Neodym:Yttrium-Aluminum-Granat-Laser (Nd:YAG-LASER)," Laryngo-Rhino-Otol. (1992) 71:388-395.

West T, "How laser surgery can help your rosacea patients," Skin & Aging. (1998) :43-46.

Wheeland RG, "Q-switched ruby laser treatment of tattoos," Am S Laser Med Surg, (1991) Abstr257.

Wheeland RG, "The progression of laser therapy for benign pigmented cutaneous lesions," Am S Laser Med Surg, (1991) Abstr261.

Wilder D, "Pulsed 1064-nm Nd:YAG laser therapy for noninvasive treatment of a massive hemangioma: case report," J Clin Laser Med Surg. (1999) 17(6):245-247.

Wilson BC, "The physics of photodynamic therapy," Phys Med Biol. (1986) 31(4):327-360.

Yano K, "Control of hair growth and follicle size by VEGF-mediated angiogenesis," J Clin Invest. (2001) 107:409-417.

Yun P, "Successful treatment of discoid lupus erthematosus utilizing the 596nm pulsed dye laser," Proc Am S Laser Med Surg. (2002) Abstr317.

Meijeriny LJT, "Limits of radial time constant to approximate thermal response in tissue," Lasers Surg Med. (1993) 13:685-687.

Mentzel T, "Cutaneous lipomatous neoplasms," Semin Diagnos Pathol. (2001) 18(4):250-257.

Miller ID, "Optical modelling of light distribution in skin tissue following laser irradiation," Lasers Surg Med. (1993) 13:565-571.

Miller TD, "The treatment of professional and amateur tattoos: a new clinical and theoretical results," Am S Laser Med Surg, (1991) Abstr256.

Milner TE, "Analysis of nonablative skin resurfacing," In: Lasers in Surgery: Advanced Characterization, Therapeutics, and Systems VII, Ed. Anderson RR (1997) 367-373, SPIE Press.

Milner TE, "Pulsed photothermal radiometry measurement of skin irradiation under nonablative laser wrinkles reduction conditions," Am S Laser Med Surg, (1997) Abstr195.

Monzon JR, "Lipolysis in adipocytes isolated from deep and subcutaneous adipose tissue," Obesity Research. (2002) 10(4):266-269.

Mooney E, "Dermatopathology and immunohistochemistry of cutaneous and systemic lupus erythematosus," J Eu Acad Dermatol Venereol. (1995) 5(1):AbstrW78.

Mordon S, "Rationale for automatic scanners in laser treatment of port wine stains," Lasers Surg Med. (1993) 13:113-123.

Moreira H, "Holmium laser thermokeratoplasty," Opthalmol. (1993) 100(5):752-761.

Morelli, J, "Tunable dye laser (577nm) treatment of port wine stains," Lasers Surg Med. (1986) 6:94-99.

Murphy GF, "Mechanisms of apoptotic regulation of follicular regression," Am J Phatol. (2001) 158(6):1899-1901.

Mutzhas MF, "A new apparatus with high radiation energy between 320-460nm: physical description and dermatological applications," J Invest Dermatol. (1981) 76:42-47.

Nakagawa H, "Ultrastructural changes in human skin after exposure to a pulsed laser," J Invest Dermatol. (1985) 84(5):396-400.

Neira R, "Fat liquefaction: effect of low-level laser energy on adipose tissue," Cosmetic. (2002) 110(3):912-922.

Newman JB, "Variable pulse Er:YAG laser skin resurfacing of perioral rhytids and side-by-side comparison with carbon dioxide laser," Lasers Surg Med. (2000) 26:208-214.

Palmer SE, "Use of Nd:YAG laser contact fiber delivery system for laparoscopic laser ovariectomy in the mare," Am S Laser Med Surg, (1992) Abstr331.

Paul BS, "The effect of temperature and other factors on selective microvasculature damage caused by pulsed dye laser," J Invest Dermatol. (1983) 81(4):333-336.

Paull RM, "An EsteLux—Epilight comparison study," Palomar Technologies <http://www.daltonmedical.nl/newsite/info.nsf/files/Este-Epi_Comparison.pdf/sfile/este-Epi_Comparison.pdf> (2002).

Pellacani G, "Variations in facial skin thickness and echogenicity with site and age," Acta Derm Venereol. (1999) 79:366-369.

Penicaud L, "The autonomic nervous system, adipose tissue plasticity, and energy balance," Nutr. (2000) 16:903-908.

Pfefer TJ, "Mechanisms of laser-induced thermal coagulation of whole blood in vitro," In: Lasers in Surgery: Advanced Characterization, Therapeutics, and Systems IX, Ed. Anderson RR (1999) 20-31, SPIE Press.

Philipp C, "Treatment of congenital vase disorder," In: Medical Applications of Lasers, Ed. Atsumi K (1994) 228-238, SPIE Press.

Phinney SD, "Human subcutaneous adipose tissue shows site-specific differences in fatty-acid composition," Am J Clin Nutr. (1994) 60:725-729.

Pickering JW, "585 nm for the laser treatment of port wine stains: a possible mechanism," Lasers Surg Med. (1991) 11:616-618.

Pierard GE, "Cellulite: from standing fat herniation to hypodermal stretch marks," Am J Dermatopathol. (2000) 22(1):34-37.

Plewig G, "A new apparatus for the delivery of high intensity UVA and UVA+UVB irradiation and some dermatological applications," Brit J Dermatol. (1978) 98:15-24.

Polla LL, "Tunable pulsed dye laser for the treatment of benign cutaneous vasculature ectasia," Dermatologica. (1987) 174:11-17.

Pottier RR, "Assessment of non-coherent light sources for photodynamic therapy," In: 5th international photodynamic association biennial meeting, Ed. Cortese DA (1995) 364-368, SPIE Press.

Pratesi R, "Potential use of incoherent and coherent light-emitting diodes (LEDs) in photomedicine," In: Laser photobiology and photomedicine, Ed. Martellucci S (1985) 296-308, plenum Press:New York.

Price VH, "Treatment of hair loss," NEJM. (1999) 341(13):964-973.

Prins JB, "Apoptosis of human adipocytes in vivo," Bioch Biophys Res Comm. (1994) 201(2):500-507.

Raulin C, "Treatment of adult port-wine stains using intense pulsed light therapy (Photoderm VL): brief initial clinical report," Derm Surg. (1997) 23:594-597.

Ramrus A, "A compact one-half MV rep-rate pulser," In: 12th International Pulsed Power Conference, (1992) 68-71, IEEE.

Ramrus A, "Design and performance of a one-half MV repetition rate pulser," In: 8th International Pulsed Power Conference, Ed. White R (1991) 982-985, IEEE.

* cited by examiner

HANDPIECE WITH RF ELECTRODE AND NON-VOLATILE MEMORY

CROSS-REFERENCE TO RELATED APPLICATIONS

This application is a continuation of U.S. Ser. No. 10/404,414 filed Mar. 31, 2003, now abandoned, which is a continuation-in-part of U.S. Ser. No. 10/400,187, filed Mar. 25, 2003, now U.S. Pat. No. 7,299,436, which is a continuation-in-part of U.S. Ser. No. 10/072,475, filed Feb. 6, 2002, now U.S. Pat. No. 7,022,121, and a continuation-in-part of U.S. Ser. No. 10/072,610, filed Feb. 6, 2002, now U.S. Pat. No. 7,141,049, both of which are continuations-in-part of U.S. Ser. No. 09/522,275, filed Mar. 9, 2000, now U.S. Pat. No. 6,413,255, which claims the benefit of U.S. Ser. No. 60/123,440, filed Mar. 9, 1999. U.S. Ser. No. 10/400,187 is also a continuation-in-part of U.S. Ser. No. 10/026,870, filed Dec. 20, 2001, now U.S. Pat. No. 6,749,624, which is a continuation of U.S. Ser. No. 09/337,015, filed Jun. 30, 1999, now U.S. Pat. No. 6,350,276, which is a continuation-in-part of U.S. Ser. No. 08/583,815, filed Jan. 5, 1996, now U.S. Pat. No. 6,241,753, U.S. Ser. No. 08/827,237, filed Mar. 28,1997, U.S. Ser. No. 08/914,681, filed Aug. 19, 1997, now U.S. Pat. No. 5,919,219, and U.S. Ser. No. 08/942,274, filed Sep. 30, 1997, now U.S. Pat. No. 6,425,912. All of the above applications are all fully incorporated herein by reference.

BACKGROUND OF THE INVENTION

1. Field of the Invention

This invention relates generally to an RF device, and more particularly to an RF electrode that includes a memory which stores information utilized to assist in providing treatment to a selected tissue site.

2. Description of Related Art

The human skin is composed of two elements: the epidermis and the underlying dermis. The epidermis with the stratum corneum serves as a biological barrier to the environment. In the basilar layer of the epidermis, pigment-forming cells called melanocytes are present. They are the main determinants of skin color.

The underlying dermis provides the main structural support of the skin. It is composed mainly of an extra-cellular protein called collagen. Collagen is produced by fibroblasts and synthesized as a triple helix with three polypeptide chains that are connected with heat labile and heat stable chemical bonds. When collagen-containing tissue is heated, alterations in the physical properties of this protein matrix occur at a characteristic temperature. The structural transition of collagen contraction occurs at a specific "shrinkage" temperature. The shrinkage and remodeling of the collagen matrix with heat is the basis for the technology. Although the technology can be deployed to effect other changes to the skin, skin appendages (sweat glands, sebaceous glands, hair follicles, etc.), or subcutaneous tissue structures.

Collagen crosslinks are either intramolecular (covalent or hydrogen bond) or intermolecular (covalent or ionic bonds). The thermal cleavage of intramolecular hydrogen crosslinks is a scalar process that is created by the balance between cleavage events and relaxation events (reforming of hydrogen bonds). No external force is required for this process to occur. As a result, intermolecular stress is created by the thermal cleavage of intramolecular hydrogen bonds. Essentially, the contraction of the tertiary structure of the molecule creates the initial intermolecular vector of contraction.

Collagen fibrils in a matrix exhibit a variety of spatial orientations. The matrix is lengthened if the sum of all vectors acts to lengthen the fibril. Contraction of the matrix is facilitated if the sum of all extrinsic vectors acts to shorten the fibril. Thermal disruption of intramolecular hydrogen bonds and mechanical cleavage of intermolecular crosslinks is also affected by relaxation events that restore preexisting configurations. However, a permanent change of molecular length will occur if crosslinks are reformed after lengthening or contraction of the collagen fibril. The continuous application of an external mechanical force will increase the probability of crosslinks forming after lengthening or contraction of the fibril.

Hydrogen bond cleavage is a quantum mechanical event that requires a threshold of energy. The amount of (intramolecular) hydrogen bond cleavage required corresponds to the combined ionic and covalent intermolecular bond strengths within the collagen fibril. Until this threshold is reached, little or no change in the quaternary structure of the collagen fibril will occur. When the intermolecular stress is adequate, cleavage of the ionic and covalent bonds will occur. Typically, the intermolecular cleavage of ionic and covalent bonds will occur with a ratcheting effect from the realignment of polar and nonpolar regions in the lengthened or contracted fibril.

Cleavage of collagen bonds also occurs at lower temperatures but at a lower rate. Low-level thermal cleavage is frequently associated with relaxation phenomena in which bonds are reformed without a net change in molecular length. An external force that mechanically cleaves the fibril will reduce the probability of relaxation phenomena and provides a means to lengthen or contract the collagen matrix at lower temperatures while reducing the potential of surface ablation.

Soft tissue remodeling is a biophysical phenomenon that occurs at cellular and molecular levels. Molecular contraction or partial denaturization of collagen involves the application of an energy source, which destabilizes the longitudinal axis of the molecule by cleaving the heat labile bonds of the triple helix. As a result, stress is created to break the intermolecular bonds of the matrix. This is essentially an immediate extra-cellular process, whereas cellular contraction requires a lag period for the migration and multiplication of fibroblasts into the wound as provided by the wound healing sequence. In higher developed animal species, the wound healing response to injury involves an initial inflammatory process that subsequently leads to the deposition of scar tissue.

The initial inflammatory response consists of the infiltration by white blood cells or leukocytes that dispose of cellular debris. Seventy-two hours later, proliferation of fibroblasts at the injured site occurs. These cells differentiate into contractile myofibroblasts, which are the source of cellular soft tissue contraction. Following cellular contraction, collagen is laid down as a static supporting matrix in the tightened soft tissue structure. The deposition and subsequent remodeling of this nascent scar matrix provides the means to alter the consistency and geometry of soft tissue for aesthetic purposes.

In light of the preceding discussion, there are a number of dermatological procedures that lend themselves to treatments which deliver thermal energy to the skin and underlying tissue to cause a contraction of collagen, and/or initiate a would healing response. Such procedures include skin remodeling/resurfacing, wrinkle removal, and treatment of the sebaceous glands, hair follicles adipose tissue and spider veins.

Currently available technologies that deliver thermal energy to the skin and underlying tissue include Radio Frequency (RF), optical (laser) and other forms of electromagnetic energy as well as ultrasound and direct heating with a hot surface. However, these technologies have a number of technical limitations and clinical issues which limit the effectiveness of the treatment and/or preclude treatment altogether.

These issues include the following: i) achieving a uniform thermal effect across a large area of tissue, ii) controlling the depth of the thermal effect to target selected tissue and prevent unwanted thermal damage to both target and non-target tissue, iii) reducing adverse tissue effects such as burns, redness blistering, iv) replacing the practice of delivery energy/treatment in a patchwork fashion with a more continuous delivery of treatment (e.g. by a sliding or painting motion), v) improving access to difficult-to-reach areas of the skin surface and vi) reducing procedure time and number of patient visits required to complete treatment. As will be discussed herein the current invention provides an apparatus for solving these and other limitations.

One of the key shortcomings of currently available RF technology for treating the skin is the edge effect phenomenon. In general, when RF energy is being applied or delivered to tissue through an electrode which is in contact with that tissue, the current concentrates around the edges of the electrode, sharp edges in particular. This effect is generally known as the edge effect. In the case of a circular disc electrode, the effect manifests as a higher current density around the perimeter of that circular disc and a relatively low current density in the center. For a square-shaped electrode there is typically a high current density around the entire perimeter, and an even higher current density at the corners.

Edge effects cause problems in treating the skin for several reasons. First, they result in a non-uniform thermal effect over the electrode surface. In various treatments of the skin, it is important to have a uniform thermal effect over a relatively large surface area, particularly for dermatological treatments. Large in this case being on the order of several square millimeters or even several square centimeters. In electrosurgical applications for cutting tissue, there typically is a point type applicator designed with the goal of getting a hot spot at that point for cutting or even coagulating tissue. However, this point design is undesirable for creating a reasonably gentle thermal effect over a large surface area. What is needed is an electrode design to deliver uniform thermal energy to skin and underlying tissue without hot spots.

A uniform thermal effect is particularly important when cooling is combined with heating in skin/tissue treatment procedure. As is discussed below, a non-uniform thermal pattern makes cooling of the skin difficult and hence the resulting treatment process as well. When heating the skin with RF energy, the tissue at the electrode surface tends to be warmest with a decrease in temperature moving deeper into the tissue. One approach to overcome this thermal gradient and create a thermal effect at a set distance away from the electrode is to cool the layers of skin that are in contact with the electrode. However, cooling of the skin is made difficult if there is a non-uniform heating pattern.

If the skin is sufficiently cooled such that there are no burns at the corners of a square or rectangular electrode, or at the perimeter of a circular disc electrode, then there will probably be overcooling in the center and there won't be any significant thermal effect (i.e. tissue heating) under the center of the electrode. Contrarily, if the cooling effect is decreased to the point where there is a good thermal effect in the center of the electrode, then there probably will not be sufficient cooling to protect tissue in contact with the edges of the electrode. As a result of these limitations, in the typical application of a standard electrode there is usually an area of non-uniform treatment and/or burns on the skin surface. So uniformity of the heating pattern is very important. It is particularly important in applications treating skin where collagen-containing layers are heated to produce a collagen contraction response for tightening of the skin. For this and related applications, if the collagen contraction and resulting skin tightening effect are non-uniform, then a medically undesirable result may occur.

There is a need for an improved RF device. There is a further need for an RF device that is suitable for cosmetic applications. There is a yet a further need for an RF device that includes a memory that stores information utilized to assist in providing treatment to a selected tissue site.

SUMMARY OF THE INVENTION

Accordingly, an object of the present invention is to provide an improved apparatus for cooling a skin surface that includes an RF electrode.

Another object of the present invention is to provide an apparatus for cooling a skin surface that includes an RF electrode and a memory that stores information utilized to assist in providing treatment to a selected tissue site.

Yet another object of the present invention is to provide an apparatus for cooling a skin surface that includes an RF electrode and a memory that stores information to facilitate operation of at least one of a cooling member, the RF electrode or an associated RF energy source.

These and other objects of the present invention are achieved in an RF device includes a support structure coupled to an RF electrode that has conductive and dielectric portions. A cooling member is coupled to the support structure and is configured to cool a back surface of the RF electrode. The cooling member is distanced from the back surface of the RF electrode. A memory is coupled to the RF electrode. The memory is configured to store information to facilitate operation of at least one of the RF electrode, the cooling member and an RF energy source.

In another embodiment of the present invention, an RF device includes a support structure coupled to an RF electrode that has conductive and dielectric portions and a flex circuit. A cooling member is coupled to the support structure and configured to cool a back surface of the RF electrode. A memory is coupled to the RF electrode. The memory is configured to store information to facilitate operation of at least one of the RF electrode, the cooling member and an RF energy source.

In another embodiment of the present invention, an RF device includes a support structure coupled to an RF electrode that has conductive and dielectric portions. First and second engagement members are formed in the body of the support structure. The first and second engagement members provide engagement and disengagement with a handpick support structure. A memory is coupled to the RF electrode. The memory is configured to store information to facilitate operation of at least one of the RF electrode and an RF energy source.

In another embodiment of the present invention, an RF device includes a support structure coupled to an RF electrode that has conductive and dielectric portions. The RF electrode is configured to be capacitively coupled when at least a portion of the RF electrode is in contact with a skin surface. A back plate is positioned at a proximal portion of the support structure. A plurality of electrical contact pads are coupled to the back plate. A memory is coupled to the RF electrode. The memory is configured to store information to facilitate operation of at least one of the RF electrode and an RF energy source.

In another embodiment of the present invention, an RF device includes a support structure coupled to an RF electrode that has conductive and dielectric portions, a tissue interface surface and an opposing back surface. A back plate is positioned at a proximal portion of the support structure. The back plate includes a front surface that faces the opposing back surface of the RF electrode, and an opposing back surface. A cooling member is provided with a channel that has distal section extending through the back plate, and a proximal section raised above the back surface of the back plate. A memory is coupled to the RF electrode. The memory is configured to store information to facilitate operation of at least one of the RF electrode, the cooling member and an RF energy source.

In another embodiment of the present invention, an RF device includes a support structure coupled to an RF electrode that has conductive and dielectric portions, a tissue interface surface and an opposing back surface. A cooling member is coupled to the RF electrode. At least a first sensor is coupled to the RF electrode. A memory is coupled to the RF electrode. The memory is configured to store information to facilitate operation of at least one of the RF electrode, the cooling member and an RF energy source.

In another embodiment of the present invention, an RF device includes a support structure coupled to an RF electrode that has conductive and dielectric portions. A cooling member is coupled to the RF electrode and is configured to cool a back surface of the RF electrode. The cooling member is distanced from the back surface of the RF electrode. A memory is coupled to the RF electrode. The memory is configured to store information to facilitate operation of at least one of the RF electrode, the cooling member and an RF energy source.

In another embodiment of the present invention, an RF device includes a support structure that defines a body of an RF device. An RF electrode is provided with conductive and dielectric portions, and a flex circuit. A cooling member is coupled to the RF electrode and is configured to cool a back surface of the RF electrode. A memory is coupled to the RF device. The memory is configured to store information to facilitate operation of at least one of the RF electrode, the cooling member and an RF energy source.

In another embodiment of the present invention, an RF device includes a support structure coupled to an RF electrode that has conductive and dielectric portions. First and second engagement members are formed in a body of the support structure. The first and second engagement members provide engagement and disengagement with a handpiece support structure. A memory is coupled to the RF electrode. The memory is configured to store information to facilitate operation of at least one of the RF electrode, the cooling member and an RF energy source.

In another embodiment of the present invention, an RF device includes a support structure coupled to an RF electrode that has conductive and dielectric portions. The RF electrode is configured to be capacatively coupled when at least a portion of the RF electrode is in contact with a skin surface. A back plate is positioned at a proximal portion of the support structure. A plurality of electrical contact pads are coupled to the back plate. A memory is coupled to the RF electrode. The memory is configured to store information to facilitate operation of at least one of the RF electrode and an RF energy source.

In another embodiment of the present invention, an RF device includes a support structure coupled to an RF electrode that has conductive and dielectric portions, a tissue interface surface and an opposing back surface. A back plate is positioned at a proximal portion of the support structure. The back plate includes a front surface that faces the opposing back surface of the RF electrode, and an opposing back surface. A cooling member has a channel with a distal section that extends through the back plate, and a proximal section raised above the back surface of the back plate. A memory is coupled to the RF electrode. The memory is configured to store information to facilitate operation of at least one of the RF electrode, the cooling member and an RF energy source.

In another embodiment of the present invention, an RF device includes a support structure coupled to an RF electrode and has conductive and dielectric portions. The RF electrode has a tissue interface surface and an opposing back surface. A cooling member is coupled to the RF electrode. At least a first sensor is coupled to the RF electrode. A memory is coupled to the RF electrode. The memory is configured to store information to facilitate operation of at least one of the RF electrode, the cooling member and an RF energy source.

In another embodiment of the present invention, an RF device includes a support structure coupled to an RF electrode that has conductive and dielectric portions, a tissue interface surface and an opposing back surface. The RF electrode has an outer edge with a geometry configured to reduce an amount of capacitively coupled area at the outer edge. A memory is coupled to the RF electrode. The memory is configured to store information to facilitate operation of at least one of the RF electrode and an RF energy source.

In another embodiment of the present invention, an RF device includes a support structure coupled to an RF electrode that has conductive and dielectric portions. The RF electrode has a tissue interface surface and an opposing back surface. At least a portion of the RF electrode has voids that reduce an amount of conductive material in the RF electrode. A memory is coupled to the RF electrode. The memory is configured to store information to facilitate operation of at least one of the RF electrode and an RF energy source.

In another embodiment of the present invention, an RF device includes a support structure coupled to an RF electrode that has conductive and dielectric portions. The RF electrode is configured to provide a controllable tissue effect on subcutaneous tissue while preserving a skin surface overlying the subcutaneous tissue. A memory is coupled to the RF electrode. The memory is configured to store information to facilitate operation of at least one of the RF electrode and an RF energy source.

In another embodiment of the present invention, an RF device includes a support structure coupled to an RF electrode. A flex circuit is coupled to the RF electrode. A memory is coupled to the RF electrode. The memory is configured to store information to facilitate operation of at least one of the RF electrode and an RF energy source.

In another embodiment of the present invention, an RF device includes a support structure coupled to an RF electrode. A flex circuit is coupled to the RF electrode. A plurality of electrical contact, pads are coupled to the flex circuit. A memory is coupled to the RF electrode. The memory is configured to store information to facilitate operation of at least one of the RF electrode and an RF energy source.

In another embodiment of the present invention, an RF device includes a support structure coupled to an RF electrode that has conductive and dielectric portions. A plurality of electrical contact pads are coupled to the RF electrode. A memory is coupled to the RF electrode. The memory is configured to store information to facilitate operation of at least one of the RF electrode and an RF energy source.

In another embodiment of the present invention, an RF device includes a support structure coupled to an RF electrode and has conductive and dielectric portions. Portions of the RF electrode have different widths. A memory is coupled to the RF electrode. The memory is configured to store information to facilitate operation of at least one of the RF electrode and an RF energy source.

In another embodiment of the present invention, an RF device includes a support structure coupled to an RF electrode that has conductive and dielectric portions. Portions of the RF electrode having different conductivities. A memory is coupled to the RF electrode. The memory is configured to store information to facilitate operation of at least one of the RF electrode and an RF energy source.

In another embodiment of the present invention, an RF device includes an RF electrode with conductive and dielectric portions. A support structure is coupled to the RF electrode. The support structure and the RF electrode form a seal where the support structure is coupled to the RF electrode. A memory is coupled to the RF electrode. The memory is configured to store information to facilitate operation of at least one of the RF electrode and an RF energy source.

In another embodiment of the present invention, an RF device includes an RF electrode that has conductive and dielectric portions. A support structure is coupled to the RF electrode. A cooling member is coupled to the RF electrode and is configured to cool a back surface of the RF electrode. The cooling member is distanced from the back surface of the RF electrode. The support structure and the RF electrode form a seal where the support structure is coupled to the RF electrode. A memory is coupled to the RF electrode. The memory is configured to store information to facilitate operation of at least one of the RF electrode, the cooling member and an RF energy source.

BRIEF DESCRIPTION OF THE DRAWINGS

FIG. 1(*b*) is a cross-sectional view of another embodiment of the RF device with a thermoelectric cooler.

FIG. 3(*b*) illustrates one embodiment of an RF electrode, that can be utilized with the present invention, with an outer edge geometry configured to reduce an amount of capacitively coupled area the outer edge.

FIG. 3(*c*) illustrates an one embodiment of an RF electrode, that can be utilized with the present invention, that has voids where there is little if any conductive material.

DETAILED DESCRIPTION

In various embodiments, the present invention provides methods for treating a tissue site. In one embodiment, an energy delivery surface of an energy delivery device is coupled to a skin surface. The coupling can be a direct, in contact, placement of the energy delivery surface of the energy delivery on the skin surface, or distanced relationship between the two without a media to conduct energy to the skin surface from the energy delivery surface of the energy delivery device. The skin surface is cooled sufficiently to create a reverse thermal gradient where a temperature of the skin surface is less than an underlying tissue. Energy is delivered from the energy delivery device to the underlying tissue area, resulting in a tissue effect at the skin surface.

Figure 1A:
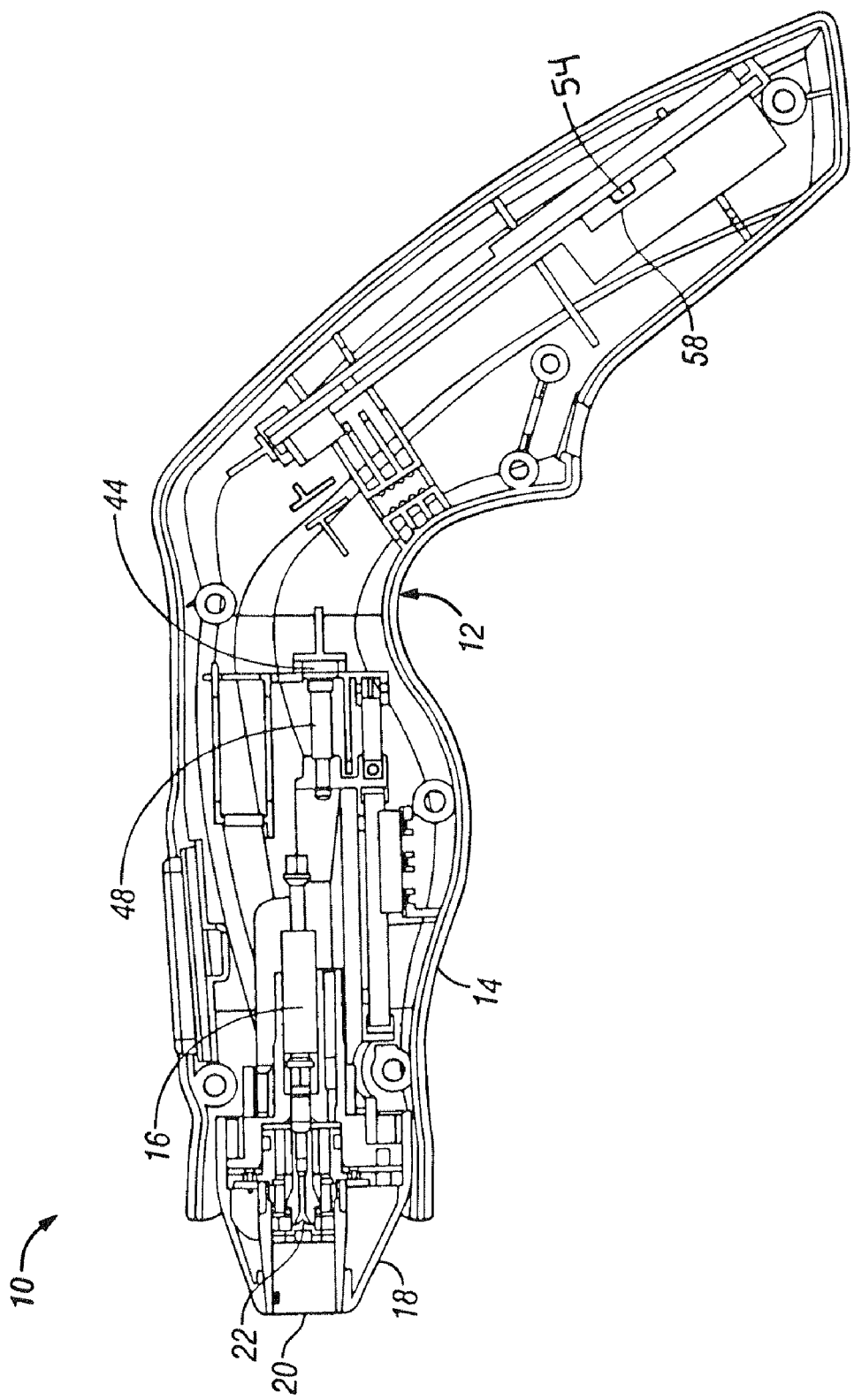
FIG. 1(*a*) is a cross-sectional view of one embodiment of the handpiece of the present invention.
Figure 1B:
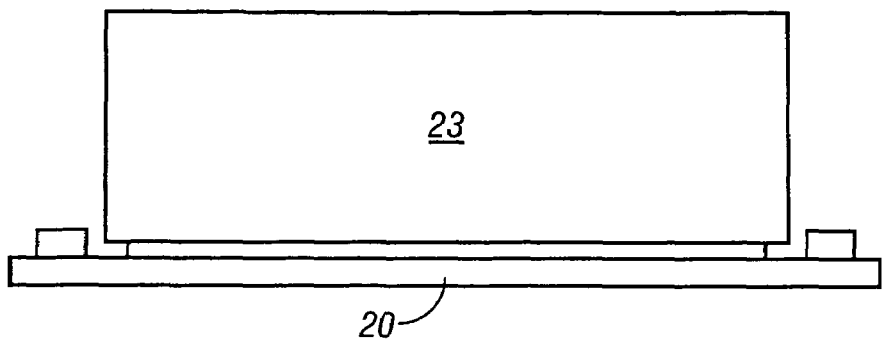

Referring now to FIG. 1(*a*), the methods of present invention can be achieved with the use of a handpiece 10. Handpiece 10 is coupled with a handpiece assembly 12 that includes a handpiece housing 14 and a cooling fluidic medium valve member 16. Handpiece housing 14 is configured to be coupled to a suitable electromagnetic energy delivery device, including but not limited to an electrode assembly 18. Electrode assembly 18 has a least one RF electrode 20 that is capacitively coupled to a skin surface when at least a portion of RF electrode 20 is in contact with the skin surface. Without limiting the scope of the present invention, RF electrode 20 can have a thickness in the range of 0.010 to 1.0 mm.

Handpiece 10 provides a more uniform thermal effect in tissue at a selected depth, while preventing or minimizing thermal damage to the skin surface and other non-target tissue. Handpiece 10 is coupled to an electromagnetic energy source, including but not limited to an RF generator, creating at least a portion of the System. RF electrode 20 can be operated either in mono-polar or bi-polar modes. Handpiece 10 is configured to reduce, or preferably eliminate edge effects and hot spots. The result is an improved aesthetic result/clinical outcome with an elimination/reduction in adverse effects and healing time.

A fluid delivery member 22 is coupled to cooling fluidic medium valve member 16. Fluid delivery member 22 and cooling fluidic medium valve member 16 collectively form a cooling fluidic medium dispensing assembly. Fluid delivery member 22 is configured to provide an atomizing delivery of a cooling fluidic medium to RF electrode 20. The atomizing delivery is a mist or fine spray. A phase transition, from liquid to gas, of the cooling fluidic medium occurs when it hits the surface of RF electrode 20. The transition from liquid to gas creates the cooling. If the transition occurs before the cooling fluidic medium hits RF electrode 20, the cooling of RF electrode 20 will not be as effective.

In another embodiment, illustrated in FIG. 1(*b*), a thermoelectric cooler 23 is utilized in place of cooling fluidic medium valve member 16 and fluid delivery member 22.

In one embodiment, the cooling fluidic medium is a cryogenic spray, commercially available from Honeywell, Morristown, N.J. A specific example of a suitable cryogenic spray is R134$A_2$, available from Refron, Inc., 38-18 33$^{rd}$ St., Long Island City, N.Y. 11101. The use of a cryogenic cooling fluidic medium provides the capability to use a number of different types of algorithms for skin treatment. For example, the cryogenic cooling fluidic medium can be applied milliseconds before and after the delivery of RF energy to the desired tissue. This is achieved with the use of cooling fluidic medium valve member 16 coupled to a cryogen supply, including but not limited to a compressed gas canister. In various embodiments, cooling fluidic medium valve member 16 can be coupled to a computer control system and/or manually controlled by the physician by means of a foot switch or similar device.

Providing a spray, or atomization, of cryogenic cooling fluidic medium is particularly suitable because it provides an availability to implement rapid on and off control. Cryogenic cooling fluidic medium allows more precise temporal control of the cooling process. This is because cooling only occurs when the refrigerant is sprayed and is in an evaporative state, the latter being a very fast short-lived event. Thus, cooling ceases rapidly after the cryogenic cooling fluidic medium is stopped. The overall effect is to confer very precise time on-off control of the cryogenic cooling fluidic medium.

Figure 2:
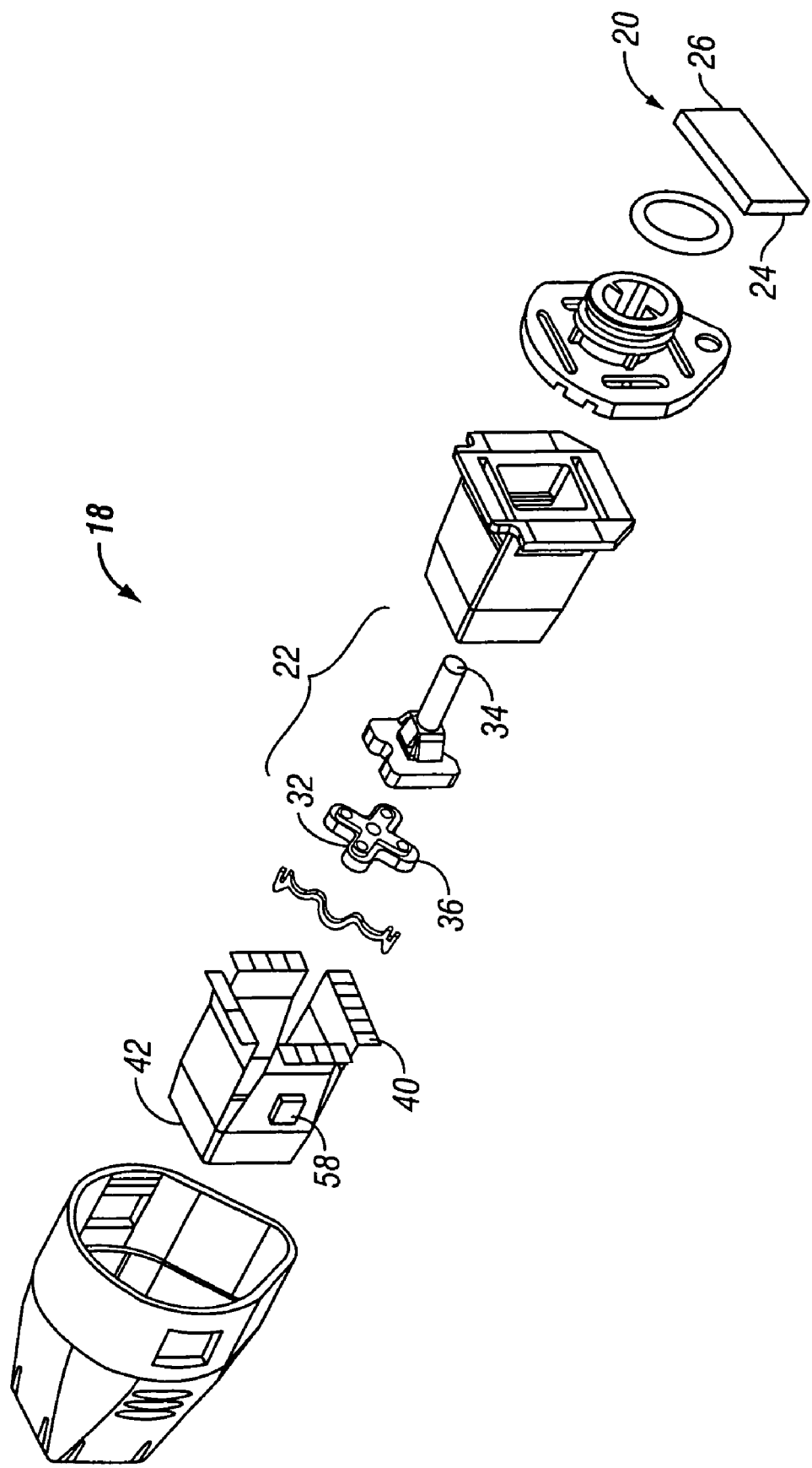
FIG. 2 is an exploded view of the FIG. 1 RF electrode assembly.

Referring now to FIG. 2, fluid delivery member 22 and thermo-electric cooler 23 can be positioned in handpiece housing 14 or electrode assembly 18. Fluid delivery member 22 is configured to controllably deliver a cooling fluidic medium. Fluid delivery member 22 and thermo-electric cooler 23 cool a back surface 24 of RF electrode 20 and maintain back surface 24 at a desired temperature. The cooling fluidic medium evaporatively cools RF electrode 20 and maintains a substantially uniform temperature of front surface 26 of RF electrode 20. Fluid delivery member 22 evaporatively cools back surface 24. Front surface 26 may or may not be flexible and conformable to the skin, but it will still have sufficient strength and/or structure to provide good thermal coupling when pressed against the skin surface.

RF electrode 20 then conductively cools a skin surface that is adjacent to a front surface 26 of RF electrode 20. Suitable fluidic media include a variety of refrigerants such as R134A and freon.

Fluid delivery member 22 is configured to controllably deliver the cooling fluidic medium to back surface 24 at substantially any orientation of front surface 26 relative to a direction of gravity. A geometry and positioning of fluid delivery member 22 is selected to provide a substantially uniform distribution of cooling fluidic medium on back surface 24. The delivery of the cooling fluidic medium can be by spray of droplets or fine mist, flooding back surface 24, and the like. Cooling occurs at the interface of the cooling fluidic medium with atmosphere, which is where evaporation occurs. If there is a thick layer of fluid on back surface 24 the heat removed from the treated skin will need to pass through the thick layer of cooling fluidic medium, increasing thermal resistance. To maximize cooling rates, it is desirable to apply a very thin layer of cooling fluidic medium. If RF electrode 20 is not horizontal, and if there is a thick layer of cooling fluidic medium, or if there are large drops of cooling fluidic medium on back surface 24, the cooling fluidic medium can run down the surface of RF electrode 20 and pool at one edge or corner, causing uneven cooling. Therefore, it is desirable to apply a thin layer of cooling fluidic medium with a fine spray. Thermo-electric cooler 23 achieves these same results but without delivering a cooling medium. Thermo-electric cooler 23 is cold on the side that is adjacent to or in contact with surface 24, while its opposing side becomes warmer.

Figure 3A:
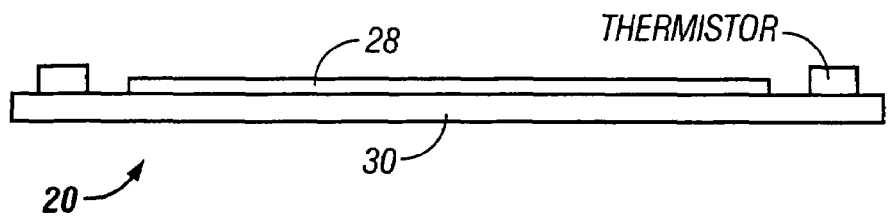
FIG. 3(*a*) is a close-up view of one embodiment of an RF electrode of the present invention.

In various embodiments, RF electrode 20, as illustrated in FIG. 3(a), has a conductive portion 28 and a dielectric portion 30. Conductive portion 28 can be a metal including but not limited to copper, gold, silver, aluminum and the like. Dielectric portion 30 can be made of a variety of different materials including but not limited to polyimide, Teflon® and the like, silicon nitride, polysilanes, polysilazanes, polyimides, Kapton and other polymers, antenna dielectrics and other dielectric materials well known in the art. Other dielectric materials include but are not limited to polymers such as polyester, silicon, sapphire, diamond, zirconium-toughened alumina (ZTA), alumina and the like. Dielectric portion 30 can be positioned around at least a portion, or the entirety of a periphery of conductive portion 28. In another embodiment, RF electrode 20 is made of a composite material, including but not limited to gold-plated copper, copper-polyimide, silicon/silicon-nitride and the like.

Dielectric portion 30 creates an increased impedance to the flow of electrical current through RF electrode 20. This increased impedance causes current to travel a path straight down through conductive portion 28 to the skin surface. Electric field edge effects, caused by a concentration of current flowing out of the edges of RF electrode 20, are reduced.

Figure 3B:
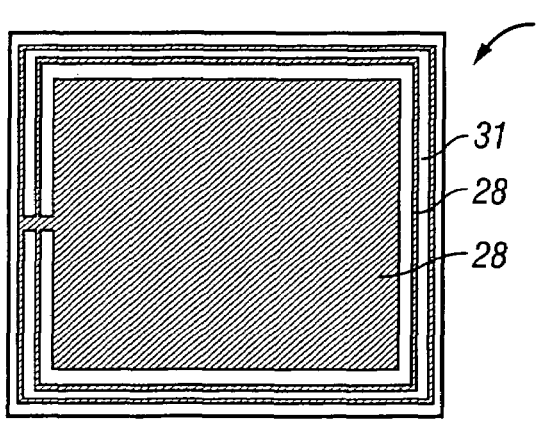
Figure 3C:
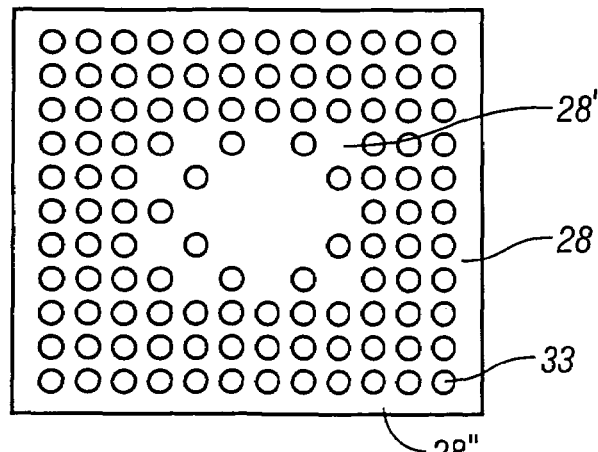

Dielectric portion 30 produces a more uniform impedance through RF electrode 20 and causes a more uniform current to flow through conductive portion 28. The resulting effect minimizes or even eliminates, edge effects around the edges of RF electrode 20. As shown in FIG. 3(c), RF electrode 20 can have voids 33 where there is little or no conductive material. Creating voids 33 in the conductive material alters the electric field. The specific configuration of voids can be used to minimize edge effect, or alter the depth, uniformity or shape of the electric field. Under a portion 28' of the RF electrode 20 with solid conductive material the electric field is deeper. Under a portion 28" of RF electrode 20 with more voids, the electric field is shallower. By combining different densities of conductive material, an RF electrode 20 is provided to match the desired heating profile.

In one embodiment, conductive portion 28 adheres to dielectric portion 30 which can be a substrate with a thickness, by way of example and without limitation, of about 0.001". This embodiment is similar to a standard flex circuit board material commercially available in the electronics industry. In this embodiment, dielectric portion 30 is in contact with the tissue, the skin, and conductive portion 28 is separated from the skin.

The thickness of the dielectric portion 30 can be decreased by growing conductive portion 28 on dielectric portion 30 using a variety of techniques, including but not limited to, sputtering, electro deposition, chemical vapor deposition, plasma deposition and other deposition techniques known in the art. Additionally, these same processes can be used to deposit dielectric portion 30 onto conductive portion 28. In one embodiment dielectric portion 30 is an oxide layer which can be grown on conductive portion 28. An oxide layer has a low thermal resistance and improves the cooling efficiency of the skin compared with many other dielectrics such as polymers.

In various embodiments, RF electrode 20 is configured to inhibit the capacitive coupling to tissue along its outside edge 31. Referring to FIG. 3(b) RF electrode 20 can have an outer edge 31 with a geometry that is configured to reduce an amount of capacitively coupled area at outer edge 31. Outer edge 31 can have less of the conductive portion 28 material. This can be achieved by different geometries, including but not limited to a scalloped geometry, and the like. The total length of outer edge 31 can be increased, with different geometries, and the total area that is capacitively coupled to tissue is reduced. This produces a reduction in energy generation around outer edge 31.

Alternatively, the dielectric material can be applied in a thicker layer at the edges, reducing the electric field at the edges. A further alternative is to configure the cooling to cool more aggressively at the edges to compensate for any electric field edge effect.

Fluid delivery member 22 has an inlet 32 and an outlet 34. Outlet 34 can have a smaller cross-sectional area than a cross-sectional area of inlet 32. In one embodiment, fluid delivery member 22 is a nozzle 36.

Cooling fluidic medium valve member 16 can be configured to provide a pulsed delivery of the cooling fluidic medium. Pulsing the delivery of cooling fluidic medium is a simple way to control the rate of cooling fluidic medium application. In one embodiment, cooling fluidic medium valve member 16 is a solenoid valve. An example of a suitable solenoid valve is a solenoid pinch valve manufactured by the N-Research Corporation, West Caldwell, N.J. If the fluid is pressurized, then opening of the valve results in fluid flow. If the fluid is maintained at a constant pressure, then the flow rate is constant and a simple open/close solenoid valve can be used, the effective flow rate being determined by the pulse duty cycle. A higher duty cycle, close to 100% increases cooling, while a lower duty cycle, closer to 0%, reduces cooling. The duty cycle can be achieved by turning on the valve for a short duration of time at a set frequency. The duration of the open time can be 1 to 50 milliseconds or longer. The frequency of pulsing can be 1 to 50 Hz or faster.

Alternatively, cooling fluidic medium flow rate can be controlled by a metering valve or controllable-rate pump such as a peristaltic pump. One advantage of pulsing is that it is easy to control using simple electronics and control algorithms.

Electrode assembly 18 is sufficiently sealed so that the cooling fluidic medium does not leak from back surface 24 onto a skin surface in contact with a front surface of RF electrode 20. This helps provide an even energy delivery through the skin surface. In one embodiment, electrode assembly 18, and more specifically RF electrode 20, has a geometry that creates a reservoir at back surface 24 to hold and gather cooling fluidic medium that has collected at back surface 24. Back surface 24 can be formed with "hospital corners" to create this reservoir. Optionally, electrode assembly 18 includes a vent that permits vaporized cooling fluidic medium to escape from electrode assembly 18.

The vent prevents pressure from building up in electrode assembly 18. The vent can be a pressure relief valve that is vented to the atmosphere or a vent line. When the cooling fluidic medium comes into contact with RF electrode 20 and evaporates, the resulting gas pressurizes the inside of electrode assembly 18. This can cause RF electrode 20 to partially inflate and bow out from front surface 26. The inflated RF electrode 20 can enhance the thermal contact with the skin and also result in some degree of conformance of RF electrode 20 to the skin surface. An electronic controller can be provided. The electronic controller sends a signal to open the vent when a programmed pressure has been reached.

Various leads 40 are coupled to RF electrode 20. One or more thermal sensors 42 are coupled to RF electrode. If will be appreciated that other sensors, including but not limited to voltage, current, power and the like, can also be included. Suitable thermal sensors 42 include but are not limited to thermocouples, thermistors, infrared photo-emitters and a thermally sensitive diode. In one embodiment, a thermal sensor 42 is positioned at each corner of RF electrode 20. A sufficient number of thermal sensors 42 are provided in order to acquire sufficient thermal data of the skin surface or the back surface 24 of the electrode 20. Thermal sensors 42 are electrically isolated from RF electrode 20. In another embodiment, at least one sensor 42 is positioned at back surface 24 of RF electrode and detects the temperature of back surface 24 in response to the delivery of cooling fluidic medium.

Thermal sensors 42 measure temperature and can provide feedback for monitoring temperature of RF electrode 20 and/or the tissue during treatment. Thermal sensors 42 can be thermistors, thermocouples, thermally sensitive diodes, capacitors, inductors or other devices for measuring temperature. Preferably, thermal sensors 42 provide electronic feedback to a microprocessor of the RF generator coupled to RF electrode 20 in order to facilitate control of the treatment.

Measurements from thermal sensors 42 can be used to help control the rate of application of cooling fluidic medium. For example, a cooling control algorithm can be used to apply cooling fluidic medium to RF electrode 20 at a high flow rate until the temperature fell below a target temperature, and then slow down or stop. A PID, or proportional-integral-differential, algorithm can be used to precisely control RF electrode 20 temperature to a predetermined value.

Thermal sensors 42 can be positioned on back surface 24 of RF electrode 20 away from the tissue. This configuration is preferable for controlling the temperature of the RF electrode 20. Alternatively, thermal sensors 42 can be positioned on front surface 26 of RF electrode 10 in direct contact with the tissue. This embodiment can be more suitable for monitoring tissue temperature. Algorithms are utilized with thermal sensors 42 to calculate a temperature profile of the treated tissue. Thermal sensors 42 can be used to develop a temperature profile of the skin which is then used for process control purposes to assure that the proper amounts of heating and cooling are delivered to achieve a desired elevated deep tissue temperature while maintaining skin tissue layers below a threshold temperature and avoid thermal injury.

The physician can use the measured temperature profile to assure that he stays within the boundary of an ideal/average profile for a given type of treatment. Thermal sensors 42 can be used for additional purposes. When the temperature of thermal sensors 42 is monitored it is possible to detect when RF electrode 20 is in contact with the skin surface. This can be achieved by detecting a direct change in temperature when skin contact is made or examining the rate of change of temperature which is affected by contact with the skin. Similarly, if there is more than one thermal sensor 42, the thermal sensors 42 can be used to detect whether a portion of RF electrode 20 is lifted or out of contact with skin. This can be important because the current density (amperes per unit area) delivered to the skin can vary if the contact area changes. In particular, if part of the surface of RF electrode 20 is not in contact with the skin, the resulting current density is higher than expected.

Referring again to FIG. 1(*a*), a force sensor 44 is also coupled to electrode assembly 18. Force sensor 44 detects an amount of force applied by electrode assembly 18, via the physician, against an applied skin surface. Force sensor 44 zeros out gravity effects of the weight of electrode assembly 18 in any orientation of front surface 26 of RF electrode 20 relative to a direction of gravity. Additionally, force sensor 44 provides an indication when RF electrode 20 is in contact with a skin surface. Force sensor 44 also provides a signal indicating that a force applied by RF electrode 20 to a contacted skin surface is, (i) above a minimum threshold or (ii) below a maximum threshold.

Figure 4:
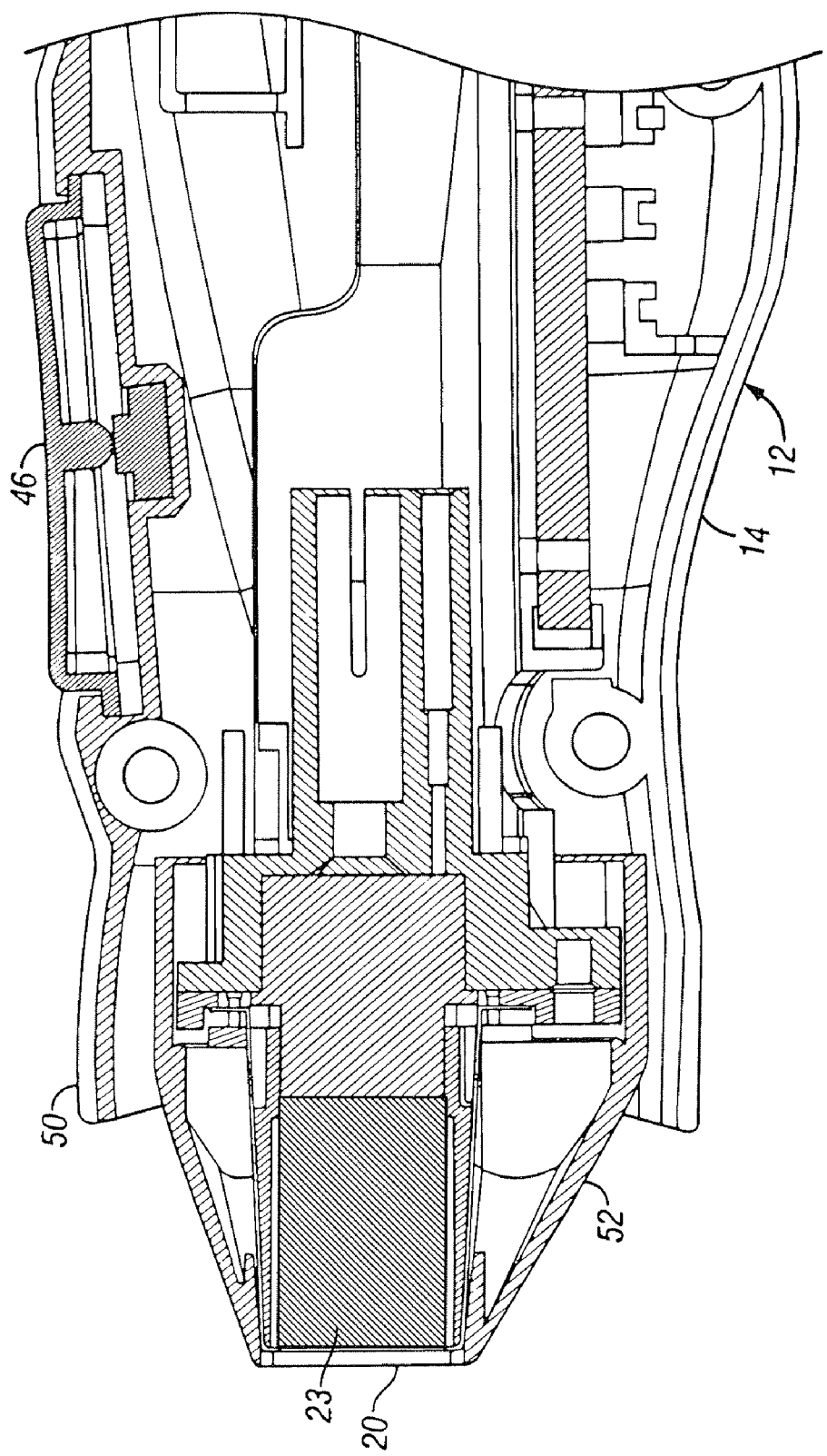
FIG. 4 is a cross-sectional view of the RF electrode assembly from FIG. 1.

As illustrated in FIG. 4, an activation button 46 is used in conjunction with the force sensor. Just prior to activating RF electrode 20, the physician holds handpiece 10 in position just off the surface of the skin. The orientation of handpiece 10 can be any angle relative to the direction of gravity. To arm handpiece 10, the physician can press activation button 46 which tares force sensor 44, by setting it to read zero. This cancels the force due to gravity in that particular treatment orientation. This method allows consistent force application of RF electrode 20 to the skin surface regardless of the angle of handpiece 10 relative to the direction of gravity.

RF electrode 20 can be a flex circuit, which can include trace components. Additionally, thermal sensor 42 and force sensor 44 can be part of the flex circuit. Further, the flex circuit can include a dielectric that forms a part of RF electrode 20.

Electrode assembly 18 can be moveably positioned within handpiece housing 12. In one embodiment, electrode assembly 18 is slideably moveable along a longitudinal axis of handpiece housing 12.

Electrode assembly 18 can be rotatably mounted in handpiece housing 12. Additionally, RF electrode 20 can be rotatably positioned in electrode assembly 18. Electrode assembly 18 can be removably coupled to handpiece housing 12 as a disposable or non-disposable RF device 52.

For purposes of this disclosure, electrode assembly 18 is the same as RF device 52. Once movably mounted to handpiece housing 12, RF device 52 can be coupled to handpiece housing 12 via force sensor 44. Force sensor 44 can be of the type that is capable of measuring both compressive and tensile forces. In other embodiments, force sensor 44 only measures compressive forces, or only measures tensile forces.

RF device 52 can be spring-loaded with a spring 48. In one embodiment, spring 48 biases RF electrode 20 in a direction toward handpiece housing 12. This pre-loads force sensor 44 and keeps RF device 52 pressed against force sensor 44. The pre-load force is tared when activation button 46 is pressed just prior to application of RF electrode 20 to the skin surface.

A shroud 50 is optionally coupled to handpiece 10. Shroud 50 serves to keep the user from touching RF device 52 during use which can cause erroneous force readings.

A memory 54 can be included with RF device 52. Memory 54 can be an EPROM and the like. Additionally, a second non-volatile memory can be included in handpiece housing 12 for purposes of storing handpiece 10 information such as but not limited to, handpiece model number or version, handpiece software version, number of RF applications that handpiece 10 has delivered, expiration date and manufacture date. Handpiece housing 12 can also contain a microprocessor 58 for purposes of acquiring and analyzing data from various sensors on handpiece housing 12 or RF device 52 including but not limited to thermal sensors 42, force sensors 44, fluid pressure gauges, switches, buttons and the like.

Microprocessor 58 can also control components on handpiece 10 including but not limited to lights, LEDs, valves, pumps or other electronic components. Microprocessor 58 can also communicate data to a microprocessor of the RF generator.

Memory 54 can be utilized to assist in a variety of different functions including but not limited to, (i) controlling an amount of current delivered by RF electrode 20, (ii) controlling energy delivery duration time of RF electrode 20, (iii) controlling a temperature of RF electrode 20 relative to a target temperature, (iv) providing a maximum number of firings of RF electrode 20, (v) providing a maximum allowed voltage that is deliverable by RF electrode 20, (vi) a history of RF electrode 20 use, (vii) a controllable duty cycle to fluid delivery member 22, (viii) providing a controllable delivery rate of cooling media delivered from fluid delivery member 22, (ix) providing an amount of time that RF electrode 20 can be used, (x) providing an amount of RF electrode 20 usage, (xi) providing a number of areas treated by RF electrode 20, (xii) providing a number of times RF electrode 20 has been moved relative to the skin surface, (xiii) providing time or date of RF electrode 20 usage, (xiv) providing a thickness of the stratum corneum, (xv) providing an amount of energy delivered by RF electrode 20, (xvi) providing a status of RF electrode 20, (xvii) providing a status of RF generator, (xviii) providing information relative to a change of tissue in response to energy delivered by RF electrode 20, (xix) providing status information of fluid delivery member 22, (xx) providing temperature information relative to fluid delivery member, (xxi) providing temperature information relative to thermoelectric cooler 23. and the like.

Figure 5:
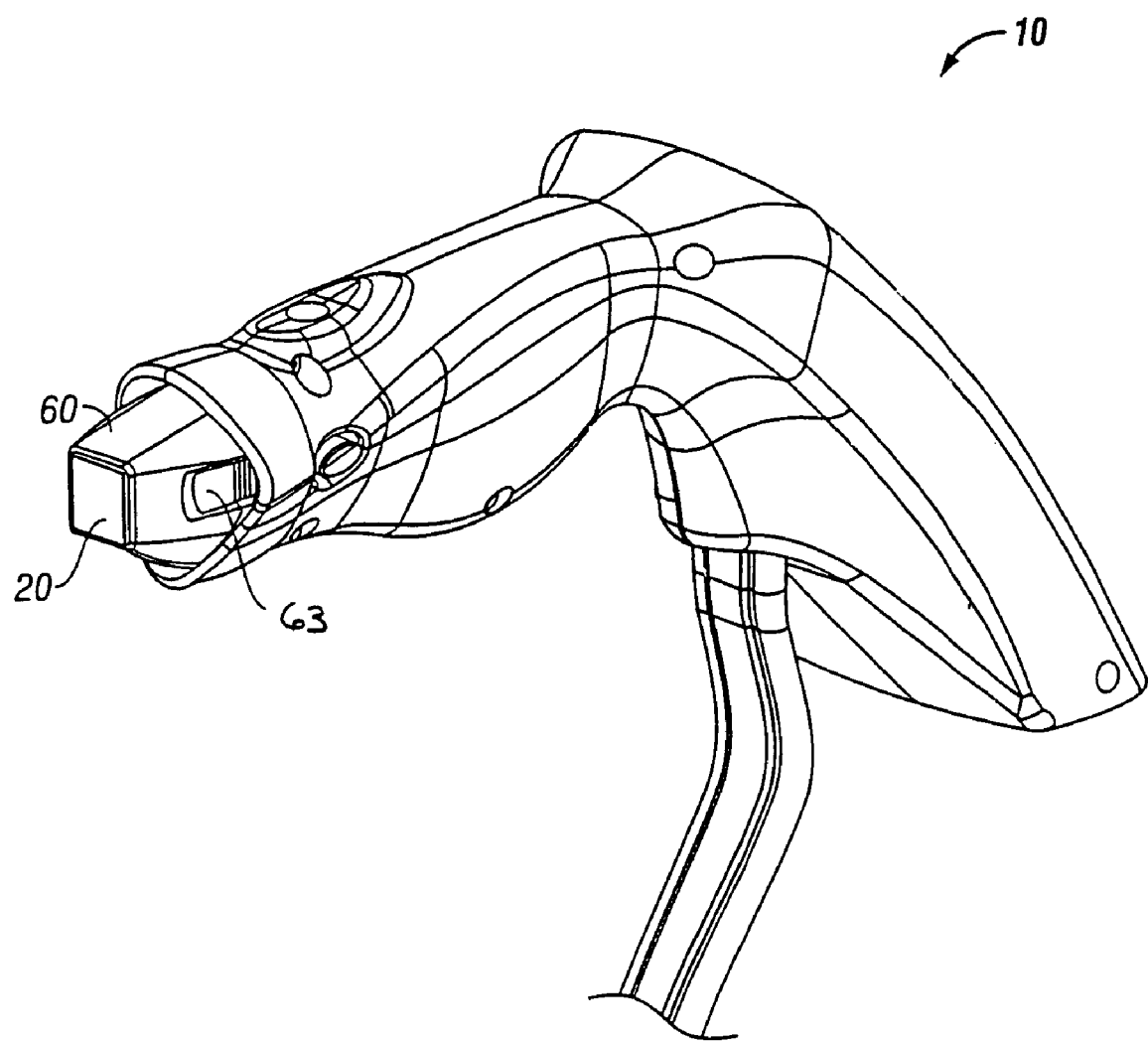
FIG. 5 is a side view of one embodiment of an RF handpiece assembly of the present invention.
Figure 6:
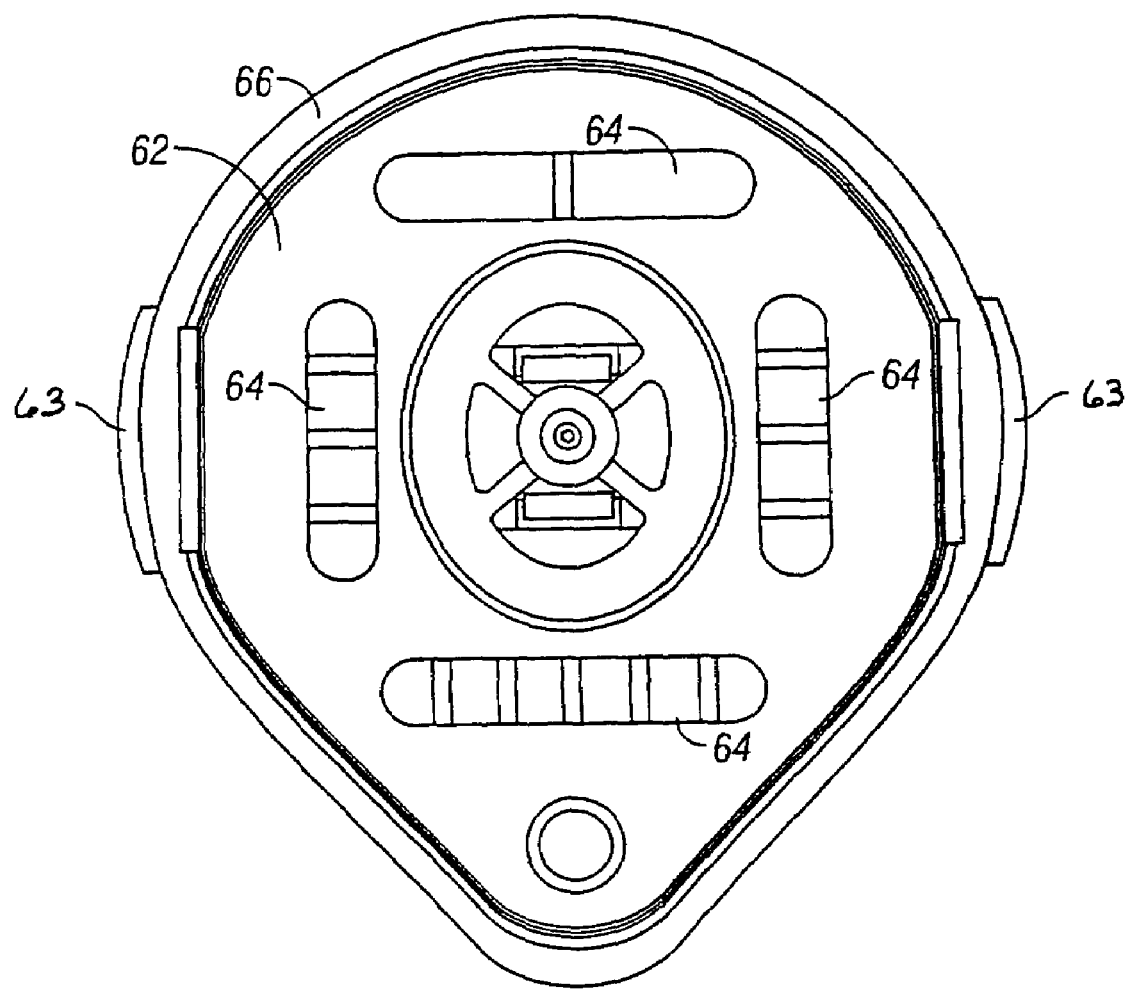
FIG. 6 is a rear view of the FIG. 5 RF electrode assembly.

Referring now to FIGS. 5 and 6, RF device 52 includes a support structure 60, including but not limited to a housing 60 that defines the body of RF device 52. RF device 52 can include a back plate 62 that is positioned at a proximal portion of support structure 60. A plurality of electrical contact pads 64 can be positioned at back plate 62. At least a portion of fluid delivery member 22 and thermoelectric cooler 23 can extend through back plate 62. Fluid delivery member 22 can be a channel with a proximal end that is raised above the back surface of back plate 62.

First and second engagement members 64 can also be formed in the body of support structure 60. Engagement members 64 provide engagement and disengagement with handpiece housing 14. Suitable engagement members 64 include but are not limited to snap members, apertures to engage with snap members of support structure 60, and the like.

Handpiece 10 can be used to deliver thermal energy to modify tissue including, but not limited to, collagen containing tissue, in the epidermal, dermal and subcutaneous tissue layers, including adipose tissue. The modification of the tissue includes modifying a physical feature of the tissue, a structure of the tissue or a physical property of the tissue. The modification can be achieved by delivering sufficient energy to modify collagen containing tissue, cause collagen shrinkage, and/or a wound healing response including the deposition of new or nascent collagen, and the like.

Handpiece 10 can be utilized for performing a number of treatments of the skin and underlying tissue including but not limited to, (i) dermal remodeling and tightening, (ii) wrinkle reduction, (iii) elastosis reduction, (iv) scar reduction, (v) sebaceous gland removal/deactivation and reduction of activity of sebaceous gland, (vi) hair follicle removal, (vii) adipose tissue remodeling/removal, (viii) spider vein removal, (ix) modify contour irregularities of a skin surface, (x) create scar or nascent collagen, (xi) reduction of bacteria activity of skin, (xii) reduction of skin pore size, (xiii) unclog skin pores and the like.

In various embodiments, handpiece 10 can be utilized in a variety of treatment processes, including but not limited to, (i) pre-cooling, before the delivery of energy to the tissue has begun, (ii) an on phase or energy delivery phase in conjunction with cooling and (iii) post cooling after the delivery of energy to tissue has stopped. Thus, in various embodiments, cooling can be delivered at different rates, e.g., during treatment phases, before, during and after delivery of the energy to the tissue site.

In one embodiment, at least a portion of the tissue site is photographed before the tissue site treatment by the System under a first set of conditions. At some time after the tissue site treatment is completed, at least a portion of the treatment site is photographed under substantially the same conditions as those of the first set of conditions.

Handpiece 10 can be used to pre-cool the surface layers of the target tissue so that when RF electrode 20 is in contact with the tissue, or prior to turning on the RF energy source, the superficial layers of the target tissue are already cooled. When RF energy source is turned on or delivery of RF to the tissue otherwise begins, resulting in heating of the tissues, the tissue that has been cooled is protected from thermal effects including thermal damage. The tissue that has not been cooled will warm up to therapeutic temperatures resulting in the desired therapeutic effect.

Pre-cooling gives time for the thermal effects of cooling to propagate down into the tissue. More specifically, pre-cooling allows the achievement of a desired tissue depth thermal profile, with a minimum desired temperature being achieved at a selectable depth. The amount or duration of pre-cooling can be used to select the depth of the protected zone of untreated tissue. Longer durations of pre-cooling produce a deeper protected zone and hence a deeper level in tissue for the start of the treatment zone. The opposite is true for shorter periods of pre-cooling. The temperature of front surface 26 of RF electrode 20 also affects the temperature profile. The colder the temperature of front surface 26, the faster and deeper the cooling, and vice verse.

Post-cooling can be important because it prevents and/or reduces heat delivered to the deeper layers from conducting upward and heating the more superficial layers possibly to therapeutic or damaging temperature range even though external energy delivery to the tissue has ceased. In order to prevent this and related thermal phenomena, it can be desirable to maintain cooling of the treatment surface for a period of time after application of the RF energy has ceased. In various embodiments, varying amounts of post cooling can be combined with real-time cooling and/or pre-cooling.

In various embodiments, handpiece 10 can be used in a varied number of pulse on-off type cooling sequences and algorithms may be employed. In one embodiment, the treatment algorithm provides for pre-cooling of the tissue by starting a spray of cryogenic cooling fluidic medium, followed by a short pulse of RF energy into the tissue. In this embodiment, the spray of cryogenic cooling fluidic medium continues while the RF energy is delivered, and is stopping shortly thereafter, e.g. on the order of milliseconds. This or another treatment sequence can be repeated again. Thus in various embodiments, the treatment sequence can include a pulsed sequence of cooling on, heat, cooling off, cooling on, heat, cool off, and with cooling and heating durations on orders of tens of milliseconds. In these embodiments, every time the surface of the tissue of the skin is cooled, heat is removed from the skin surface. Cryogenic cooling fluidic medium spray duration, and intervals between sprays, can be in the tens of milliseconds ranges, which allows surface cooling while still delivering the desired thermal effect into the deeper target tissue.

In various embodiments, the target tissue zone for therapy, also called therapeutic zone or thermal effect zone, can be at a tissue depth from approximately 100 μm beneath the surface of the skin down to as deep as 10 millimeters, depending upon the type of treatment. For treatments involving collagen contraction, it can be desirable to cool both the epidermis and the superficial layers of the dermis of the skin that lies beneath the epidermis, to a cooled depth range between 100 μm two millimeters. Different treatment algorithms can incorporate different amounts of pre-cooling, heating and post cooling phases in order to produce a desired tissue effect at a desired depth.

Various duty cycles, on and off times, of cooling and heating are utilized depending on the type of treatment. The cooling and heating duty cycles can be controlled and dynamically varied by an electronic control system known in the art. Specifically the control system can be used to control cooling fluidic medium valve member 16 and the RF power source.

Figure 7:
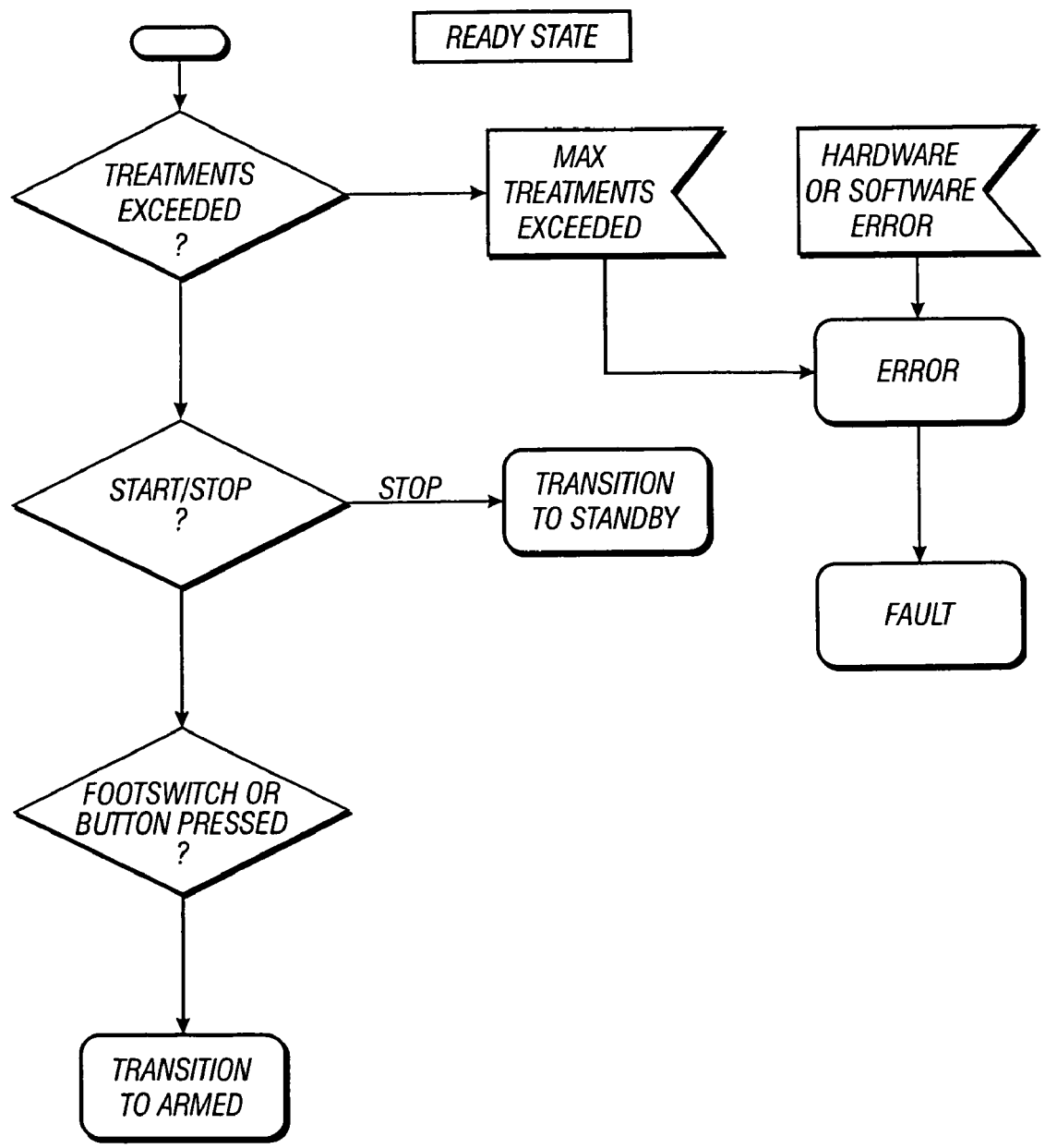
FIG. 7 is a flow chart that illustrates one embodiment of a ready state of a handpiece and its associated electromagnetic energy source (the "System").

In one embodiment, handpiece 10 is utilized in a variety of different states, including but not limited to, ready, armed, active, standby and the like. The ready state is illustrated in FIG. 7, where in one embodiment memory 54 is checked to see in the maximum treatment and/or the maximum number of treatments has been exceeded. If so, then there is an error state and a signal is provide to the physician. If neither one has been exceeded, and activation button 46 has not been pressed, then there is a wait until activation button 46, or an associated footswitch, is activated. It either one is activated, then the System proceeds to the armed state.

Figure 8:
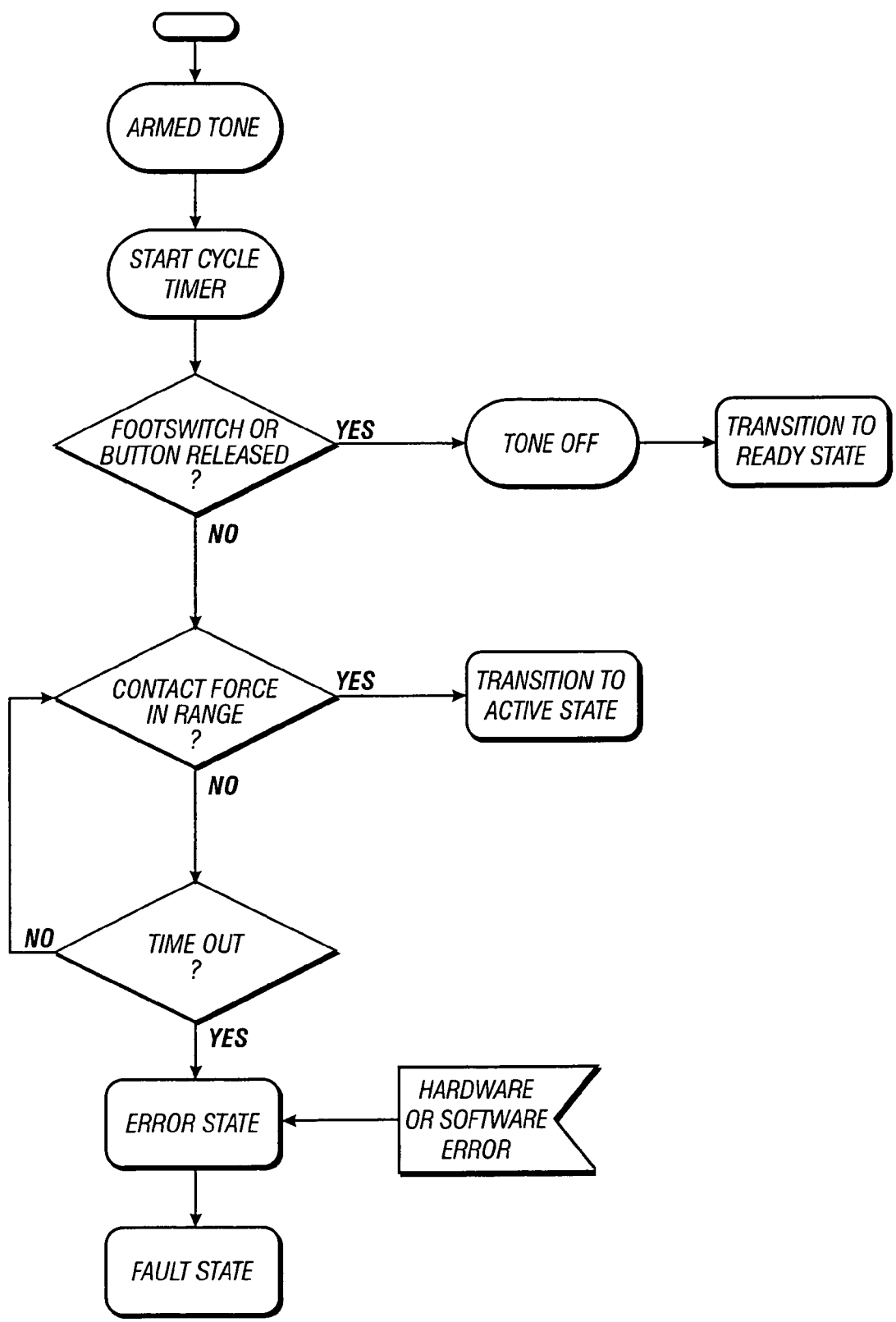
FIG. 8 is a flow chart that illustrates one embodiment of an armed state
of the System.

In the armed state, shown in FIG. 8, an armed tone can be provided, and in one embodiment three seconds are allowed for the physician to cause handpiece 10 to become coupled to a skin surface, which can be direct physical contact with the skin surface of the patient. If more than the allotted time has passed, then the System is in an error state. Force sensor 44 is used to determine when there is contact by handpiece 10 with the patient. If there is the proper amount of force applied by handpiece 10, then there is a transition to the active state.

Figure 9:
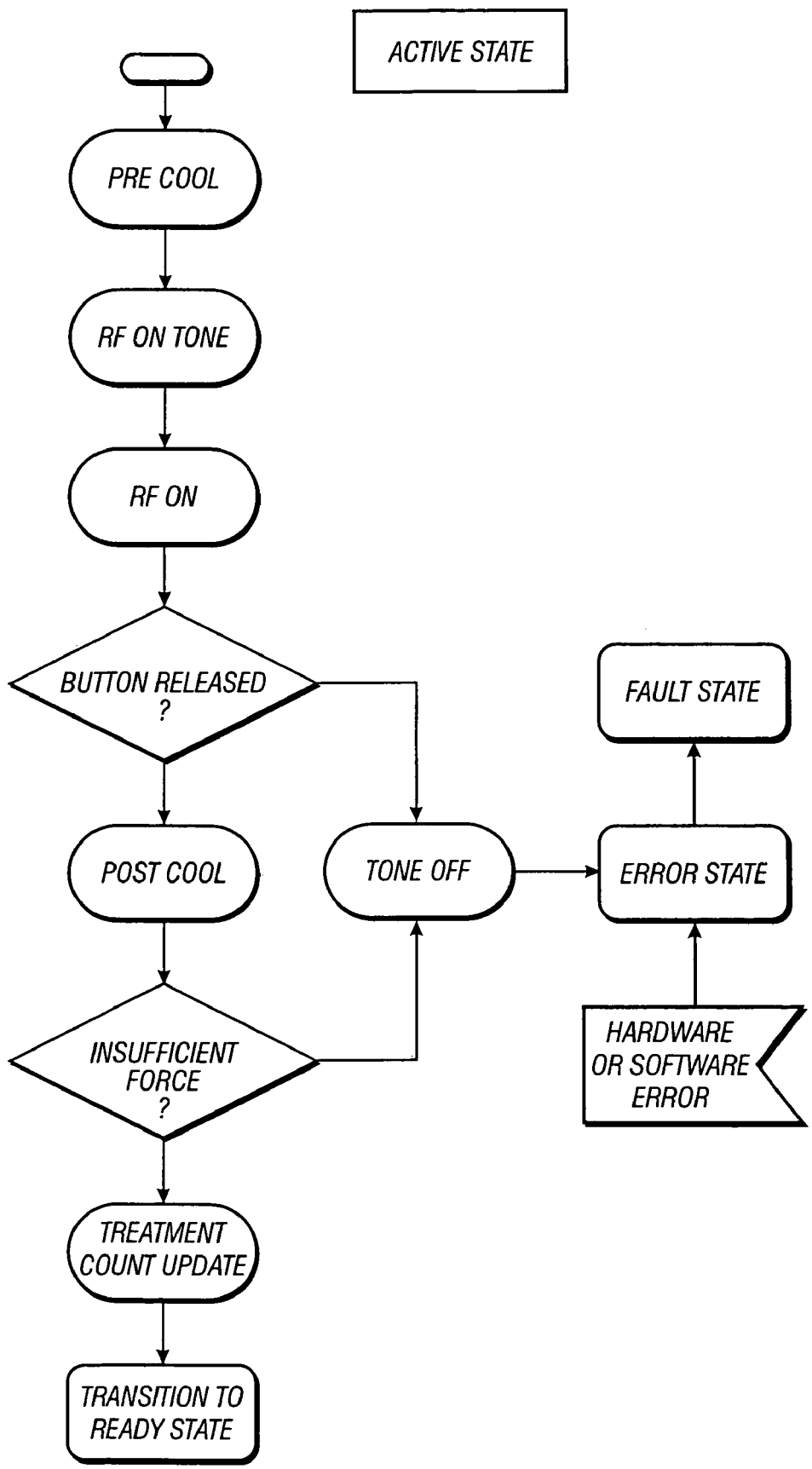
FIG. 9 is a flow chart that illustrates one embodiment of an active state of the System.

As illustrated in FIG. 9, the active begins when there is actual contact by handpiece 10 with the patient. A pre-cool is first applied to the skin surface. Electromagnetic energy, such as RF, is then delivered. If activation button 46 is released a tone or other indicator can go off and the System is again in an error state. This can occur at any time. Following delivery of electromagnetic energy, there is a post cooling state. The levels of cooling delivered to the skin surface at pre-cooling, during electromagnetic energy delivery, and post-cooling, can each be different.

Figure 10:
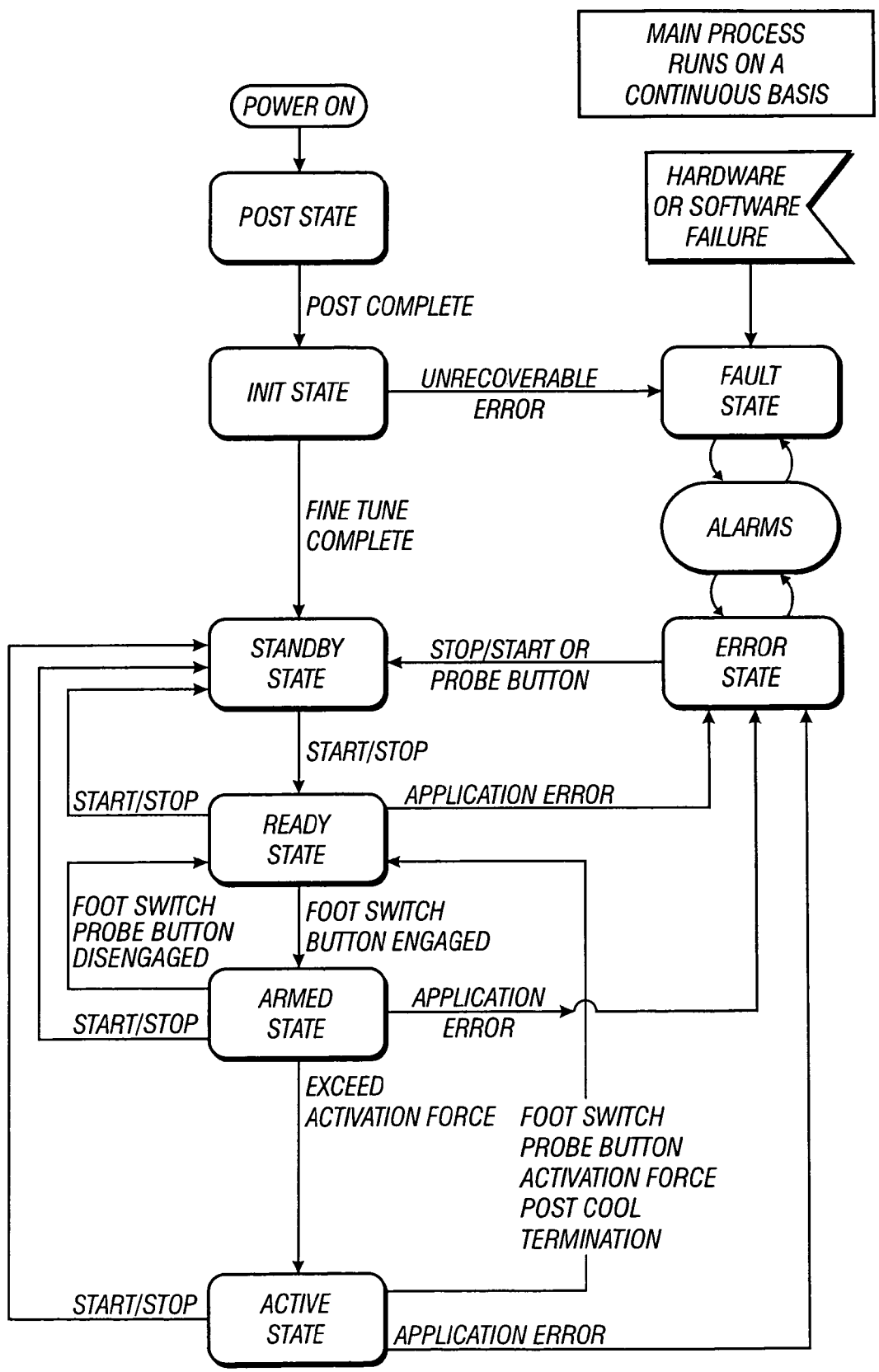
FIG. 10 is a flow chart that illustrates one embodiment of a main control loop that can be utilized with the present invention.

FIG. 10 illustrates an embodiment where a main control loop is provided that self tests the System. Following the self test, there is an initialization of the System, followed by a fine tuning, and then the System is prepared for the ready state.

Figure 11:
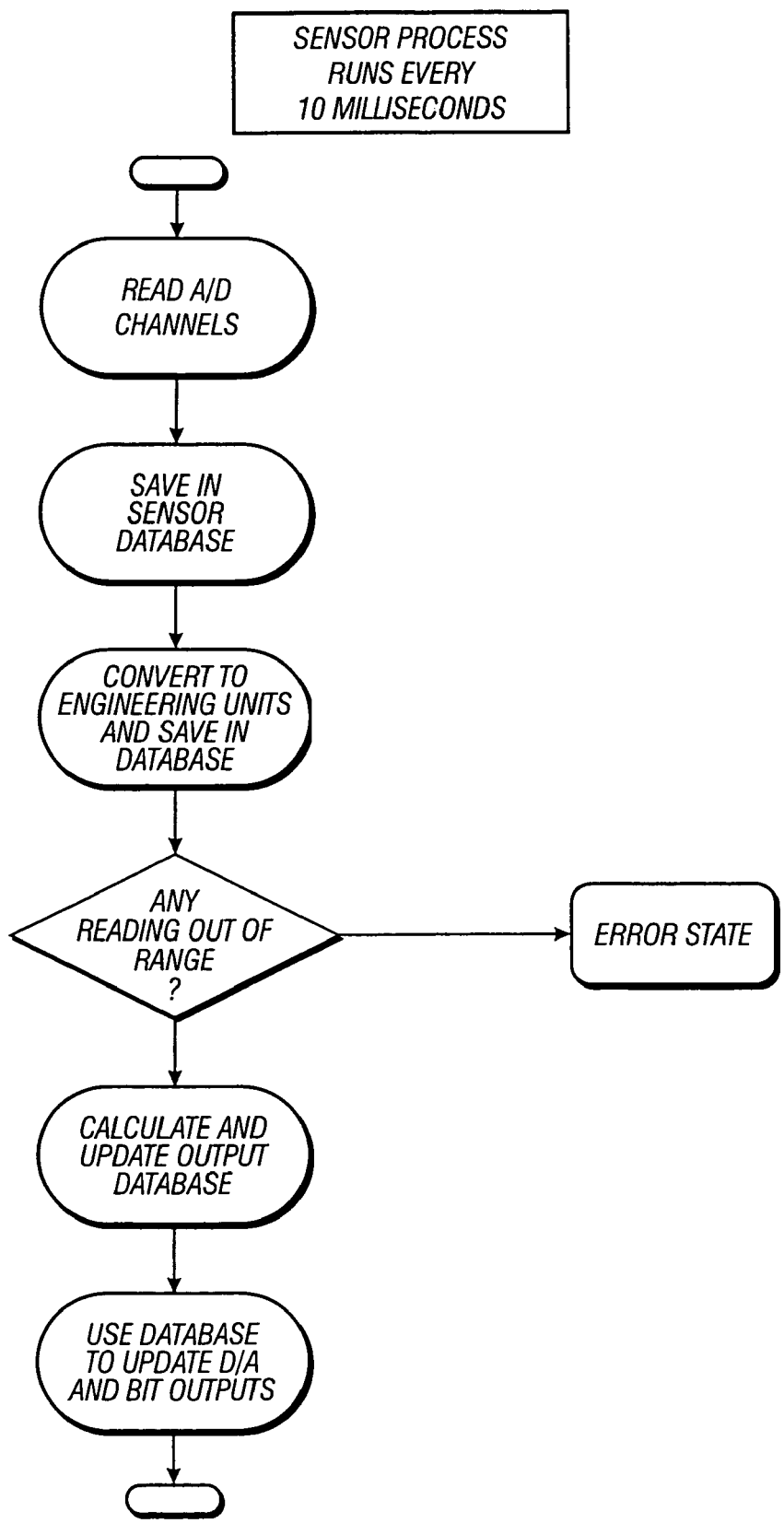
FIG. 11 is a flow chart that illustrates how the System of the present invention can check the channels of the associated sensors utilized with the present invention.
Figure 12:
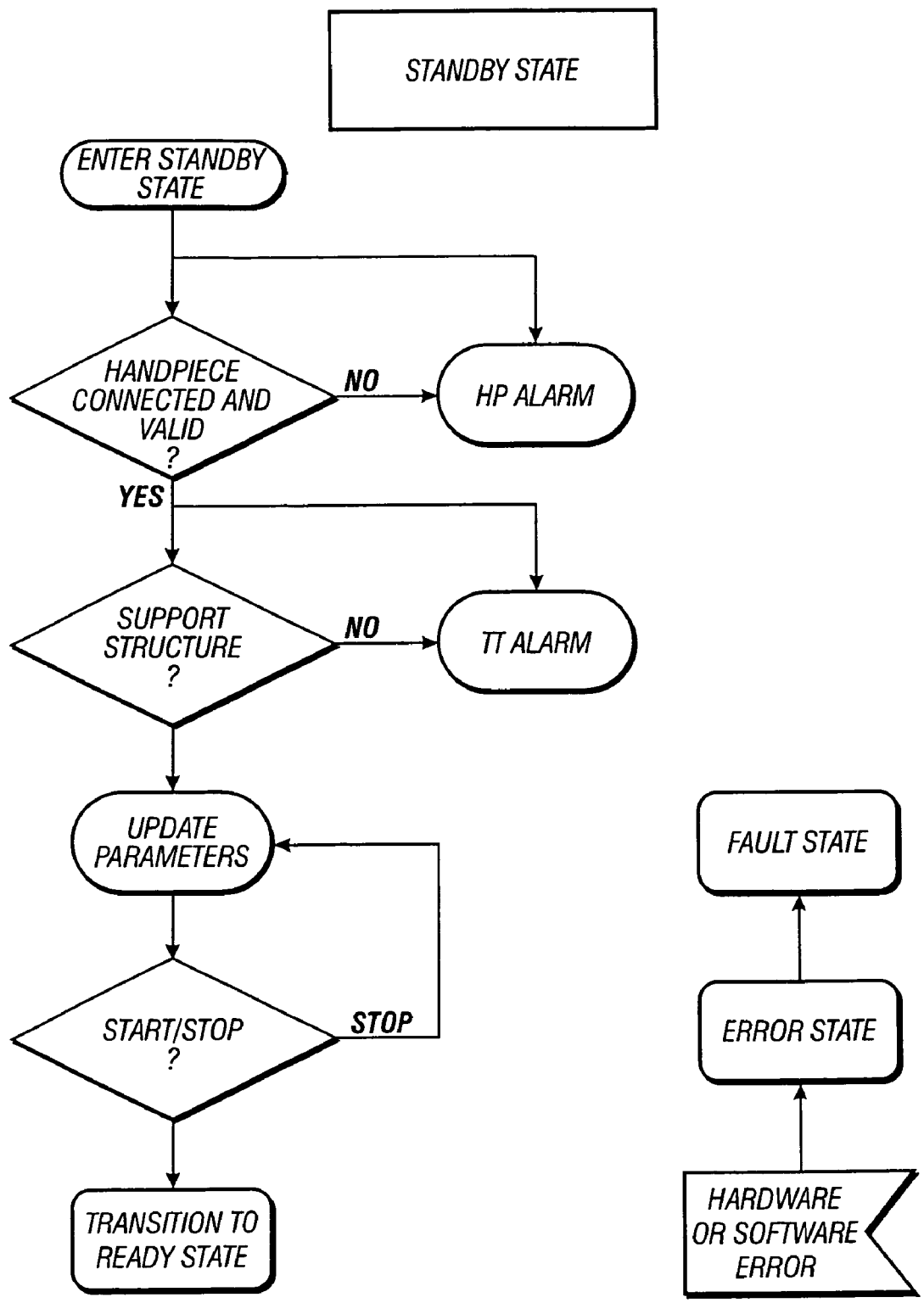
FIG. 12 is a flow chart that illustrates one embodiment of an active state of the System.

As illustrated in FIG. 11, all channels from the sensors, including but not limited to voltage, current power, temperature, and the like, are read. An updated set of current values is created. Checks are then made, as illustrated in FIG. 12, to make sure that handpiece 10 is connected to the electromagnetic energy source, and that the particular handpiece 10 is a valid one suitable for use with the electromagnetic energy source. A check is also made that support structure 60 is connected and also valid, e.g., that the support structure 60 is a suitable for use with handpiece 10 and the electromagnetic energy source. The parameters of a treatment tip associated with support structure are then updated, followed by transition to the ready state when activation button 46 or the footswitch is depressed.

Figure 13:
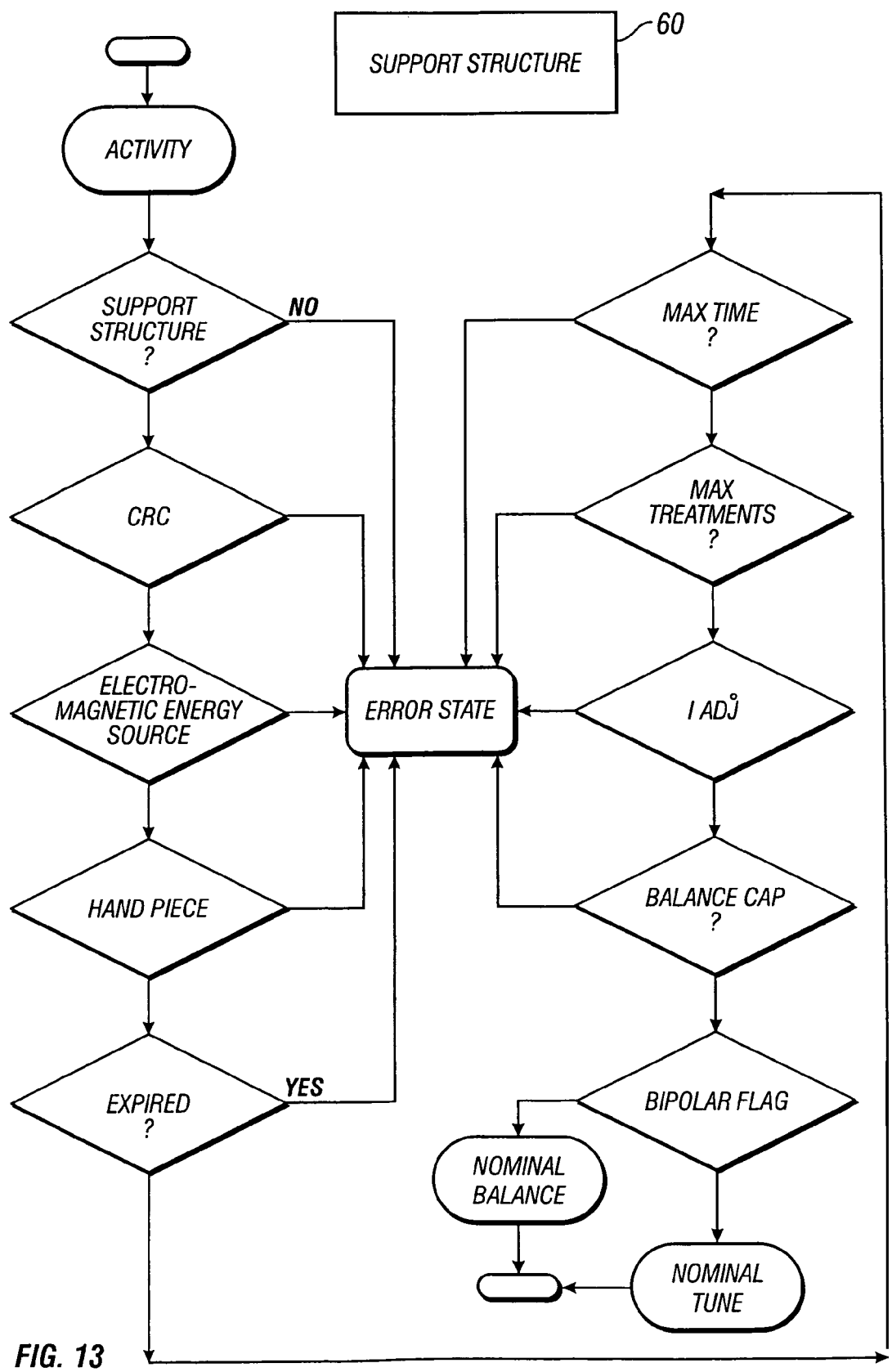
FIG. 13 is a flow chart that illustrates one embodiment of checking a support structure of the present invention.

Referring now to FIG. 13, support structure is checked to make sure that it is connected. The CRC of a memory code of memory 54 is also checked. Checks are also made to make sure that the electromagnetic energy source, and handpiece 10 are acceptable devices. If there is expiration of any of the devices, including but not limited to support structure 60, or a device is not acceptable, the System is in an error state.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An electrode assembly for use with an RF generator and a handpiece connected to the RF generator, the electrode assembly comprising:
   a support structure configured to be removably coupled with the handpiece;
   an RF electrode coupled to the support structure, the RF electrode including a back surface, a conductive portion electrically connected by the handpiece with the RF generator, and a dielectric portion;
   a cooling member coupled to the support structure, the cooling member configured to cool the back surface of the RF electrode, and the cooling member distanced from the back surface of the RF electrode; and
   a non-volatile memory coupled to the RF electrode or to the support structure, the memory configured to store information relating to at least one of the RF electrode, the cooling member, or the RF generator.

2. The electrode assembly of claim 1, wherein the non-volatile memory is configured to store an amount of current delivered by the RF electrode.

3. The electrode assembly of claim 1, wherein the non-volatile memory is configured to store energy delivery duration time of the RF electrode.

4. The electrode assembly of claim 1, wherein the non-volatile memory is configured to store a temperature of the RF electrode relative to a target temperature.

5. The electrode assembly of claim 1, wherein the non-volatile memory is configured to store a maximum number of firings of the RF electrode.

6. The electrode assembly of claim 1, wherein the non-volatile memory is configured to store a maximum allowed voltage that is deliverable by the RF electrode.

7. The electrode assembly of claim 1, wherein the non-volatile memory is configured to store a history of RF electrode use.

8. The electrode assembly of claim 1, wherein the non-volatile memory is configured to store a controllable duty cycle to cooling member.

9. The electrode assembly of claim 1, wherein the non-volatile memory is configured to store a controllable delivery rate of cooling delivered from cooling member.

10. The electrode assembly of claim 1, wherein the non-volatile memory is configured to store an amount of time that the RF electrode can be used.

11. The electrode assembly of claim 1, wherein the non-volatile memory is configured to store an amount of RF electrode usage.

12. The electrode assembly of claim 1, wherein the non-volatile memory is configured to store a number of areas treated by the RF electrode.

13. The electrode assembly of claim 1, wherein the non-volatile memory is configured to store a number of times the RF electrode has been moved relative to the skin surface.

14. The electrode assembly of claim 1, wherein the non-volatile memory is configured to store at least one of time or date RF electrode usage.

15. The electrode assembly of claim 1, wherein the non-volatile memory is configured to store a thickness of the stratum corneum.

16. The electrode assembly of claim 1, wherein the non-volatile memory is configured to store an amount of energy delivered by the RF electrode.

17. The electrode assembly of claim 1, wherein the non-volatile memory is configured to store a status of the RF electrode.

18. The electrode assembly of claim 1, wherein the non-volatile memory is configured to store a status of an RF energy system coupled to the RF electrode.

19. The electrode assembly of claim 1, wherein the non-volatile memory is configured to store information relative to a change of tissue in response to energy delivered by the RF electrode.

20. An electrode assembly for use with a handpiece that is connected with an RF generator, the electrode assembly comprising:
   a support structure configured to be removably coupled with the handpiece;
   an RF electrode coupled to the support structure, the RF electrode including a back surface, a conductive portion electrically connected by the handpiece with the RF generator, a dielectric portion, and a flex circuit;
   a cooling member coupled to the RF electrode, the cooling member configured to cool a back surface of the RF electrode; and
   a non-volatile memory coupled to the RF electrode or to the support structure, the memory configured to store information relating to at least one of the RF electrode, the cooling member, or the RF generator.

* * * * *

UNITED STATES PATENT AND TRADEMARK OFFICE
CERTIFICATE OF CORRECTION

PATENT NO. : 7,481,809 B2
APPLICATION NO. : 11/158286
DATED : January 27, 2009
INVENTOR(S) : Roger A. Stern et al.

It is certified that error appears in the above-identified patent and that said Letters Patent is hereby corrected as shown below:

On the Title Page
Under Item 56 "References Cited", on page 4, in the first column, under "Other Publications":
in line 64, change "Telangieclasia" to --Telangiectasia--
in line 67, change "OPtics" to --Optics--
in line 68, change "Telangiestasia" to --Telangiectasia--
in line 70, change "Nanablative" to --Nonablative--.

On the Title Page
Under Item 56 "References Cited", on page 4, in the second column, under "Other Publications":
in line 18, change "istense" to --intense--
in line 33, after "rabbit", insert --Achilles--
in line 72, before "intense", insert --An--.

On the Title Page
Under Item 56 "References Cited", on page 5, in the first column, under "Other Publications":
in line 62, change "damages" to --damaged--.

On the Title Page
Under Item 56 "References Cited", on page 5, in the second column, under "Other Publications":
in line 20, change "decortive" to --decorative--
in line 22, change "Appelberg" to --Apfelberg--
in line 23, change "lipsuction" to --liposuction--
in line 50, change "MV" to --MVI--.

On the Title Page
Under Item 56 "References Cited", on page 6, in the second column, under "Other Publications":
in line 12, change "Geronamus" to --Geronemus--.

UNITED STATES PATENT AND TRADEMARK OFFICE
CERTIFICATE OF CORRECTION

PATENT NO. : 7,481,809 B2
APPLICATION NO. : 11/158286
DATED : January 27, 2009
INVENTOR(S) : Roger A. Stern et al.

It is certified that error appears in the above-identified patent and that said Letters Patent is hereby corrected as shown below:

On the Title Page
Under Item 56 "References Cited", on page 7, in the first column, under "Other Publications":
in line 10, change "photodamages" to --photodamaged--.

On the Title Page
Under Item 56 "References Cited", on page 8, in the first column, under "Other Publications":
in line 15, after "and" insert --rubber band--.

On the Title Page
Under Item 56 "References Cited", on page 8, in the second column, under "Other Publications":
in line 1, after "laser" insert --irradiated--
in line 28, before "new" delete "a".

On the Title Page
Under Item 56 "References Cited", on page 9, in the first column, under "Other Publications":
in line 5, change "vase disorder" to --vascular disorders--
in line 6, change "1994" to --1993--.

In column 2, line 59, change "would" to --wound--.

In column 3:
in line 9, after "redness", insert --,--
in line 15, after "herein" insert --,--.

In column 4, line 9, after "yet" delete "a".

In column 7, line 60, after "state" delete the hard return.

UNITED STATES PATENT AND TRADEMARK OFFICE
CERTIFICATE OF CORRECTION

PATENT NO. : 7,481,809 B2
APPLICATION NO. : 11/158286
DATED : January 27, 2009
INVENTOR(S) : Roger A. Stern et al.

It is certified that error appears in the above-identified patent and that said Letters Patent is hereby corrected as shown below:

In column 11, line 57, change "if" to --it--.

In column 15, line 20, change "verse" to --versa--.

Signed and Sealed this

Twenty-second Day of December, 2009

David J. Kappos
*Director of the United States Patent and Trademark Office*